(12) United States Patent
Tobita et al.

(10) Patent No.: US 7,901,342 B2
(45) Date of Patent: *Mar. 8, 2011

(54) CENTRIFUGAL SEPARATOR WITH STERILIZING APPARATUS

(75) Inventors: Yoshinori Tobita, Ibaraki (JP);
Masaharu Aizawa, Ibaraki (JP);
Katsunori Akatsu, Ibaraki (JP);
Tomohiro Koizumi, Ibaraki (JP)

(73) Assignee: Hitachi Koki Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/477,258

(22) Filed: Jun. 3, 2009

(65) Prior Publication Data
US 2009/0239729 A1  Sep. 24, 2009

Related U.S. Application Data

(63) Continuation of application No. 11/175,375, filed on Jul. 7, 2005, now Pat. No. 7,591,775.

(30) Foreign Application Priority Data

Jul. 8, 2004 (JP) ............................. P2004-201329

(51) Int. Cl.
*B04B 15/02* (2006.01)
*B04B 15/06* (2006.01)
*B04B 15/08* (2006.01)

(52) U.S. Cl. ............... 494/14; 494/15; 494/25; 494/26; 494/27; 494/30; 494/61

(58) Field of Classification Search .............. 494/11–15, 494/23–30, 35, 38, 39, 42, 43, 85, 61; 422/26
See application file for complete search history.

(56) References Cited

U.S. PATENT DOCUMENTS

| | | | | | |
|---|---|---|---|---|---|
| 3,007,629 | A | * | 11/1961 | Boyland | 494/42 |
| 3,108,955 | A | * | 10/1963 | Boyland | 494/74 |
| 3,430,849 | A | * | 3/1969 | Nunley et al. | 494/12 |
| 3,501,091 | A | * | 3/1970 | Yoshitoshi et al. | 494/25 |
| 3,598,304 | A | * | 8/1971 | Hemfort | 494/25 |
| 4,244,513 | A | * | 1/1981 | Fayer et al. | 494/10 |
| 5,356,365 | A | * | 10/1994 | Brierton | 494/14 |

(Continued)

FOREIGN PATENT DOCUMENTS

EP            215585 A1 *  3/1987

(Continued)

OTHER PUBLICATIONS

United States Office Action issued in U.S. Appl. No. 12/901,032 dated Dec. 3, 2010.

*Primary Examiner* — Charles E Cooley
(74) *Attorney, Agent, or Firm* — McDermott Will & Emery LLP

(57) ABSTRACT

A centrifugal separator includes a sample line and a rotating apparatus portion including a rotor that has a rotor chamber. The centrifugal separator centrifugally separates a sample by supplying the sample from the sample line into the rotor and driving to rotate the rotor in the rotor chamber and discharges the centrifugally separated sample from the rotor via the sample line. The centrifugal separator includes a sterilizing apparatus for sterilizing at least a portion with which the sample is brought into contact by making a sterilizing fluid flow through the sample line.

6 Claims, 15 Drawing Sheets

U.S. PATENT DOCUMENTS

| | | | |
|---|---|---|---|
| 6,800,053 B2 * | 10/2004 | Fox | 494/1 |
| 7,144,361 B2 * | 12/2006 | Aizawa et al. | 494/38 |
| 7,396,324 B2 * | 7/2008 | Tetsu et al. | 494/7 |
| 7,591,775 B2 * | 9/2009 | Tobita et al. | 494/14 |
| 7,794,383 B2 * | 9/2010 | Tetsu et al. | 494/7 |
| 2004/0157718 A1 * | 8/2004 | Fox | 494/1 |
| 2004/0214711 A1 * | 10/2004 | Aizawa et al. | 494/79 |
| 2005/0107235 A1 * | 5/2005 | Tetsu et al. | 494/10 |
| 2006/0009341 A1 * | 1/2006 | Tobita et al. | 494/14 |
| 2008/0300124 A1 * | 12/2008 | Akatsu et al. | 494/14 |
| 2009/0239729 A1 * | 9/2009 | Tobita et al. | 494/14 |
| 2010/0075823 A1 | 3/2010 | Toi et al. | |

FOREIGN PATENT DOCUMENTS

| | | | |
|---|---|---|---|
| JP | 59090649 | | 5/1984 |
| JP | 62027055 | | 2/1987 |
| JP | 02071858 A | * | 3/1990 |
| JP | 02131154 | | 5/1990 |
| JP | 02290267 | | 11/1990 |
| JP | 04145969 | | 5/1992 |
| JP | 2000042449 | | 2/2000 |
| JP | 2002527149 | | 8/2002 |
| JP | 2002307469 | | 10/2002 |
| JP | 2006021121 A | * | 1/2006 |
| JP | 2006-247610 A | | 9/2006 |
| JP | 2007125450 | | 5/2007 |
| WO | 0021591 | | 4/2000 |

* cited by examiner

CENTRIFUGAL SEPARATOR WITH STERILIZING APPARATUS

The present application is a continuation of application Ser. No. 11/175,375, filed Jul. 7, 2005, now U.S. Pat. No. 7,591,775 B2, the contents of which are incorporated herein by reference.

BACKGROUND OF THE INVENTION

The present invention relates to a centrifugal separator for centrifugally separating a sample at inside of a rotor rotated at high speed in a rotor chamber.

FIG. 14 and FIG. 15 show a background art of a centrifugal separator of this kind.

That is, FIG. 14 is a front view of a centrifugal separator of a background art, FIG. 15 is a side view showing operation of attaching and detaching a rotor in the centrifugal separator, and a centrifugal separator 1' of the illustrated example is constituted by a rotating apparatus portion 10, a sample injecting apparatus 100' and a control apparatus portion 200 arranged on both sides thereof as shown by FIG. 14.

The rotating apparatus portion 10 is provided with a chamber 12 in a cylindrical shape on a base 11 fixed onto a floor face 2 by a plurality of pieces of bolts 3, and a rotor 13 in a cylindrical shape shown in FIG. 15 is rotatably set to be inserted into the chamber 12. Further, an upper rotating shaft 14 and a lower rotating shaft 15 are respectively extended vertically upward and downward from the rotor 13, and the upper rotating shaft 14 is connected to a drive portion 30 installed on an upper plate 16 in a shape of a circular plate. Further, the lower rotating shaft 15 is rotatably supported by a lower bearing portion 50 fixedly provided to the base 11. Further, the drive portion 30 is provided with an electric motor, not illustrated, as a drive source, the upper rotating shaft 14 is inserted to be fixedly attached to an output shaft (motor shaft) of the electric motor, and a path (not illustrated) in a shape of a circular hole is penetrated through the upper rotating shaft 14 and the lower rotating shaft 15 for passing a sample.

Further, the rotating apparatus portion 10 is erected with a pair of left and right vertical lifts 70 which are hydraulically moved up and down on a back side (left side of FIG. 15) of the chamber 12, and a pair of left and right horizontal lifts 80 are horizontally attached between the vertical lifts 70. Here, each of the horizontal lifts 80 is hydraulically moved forward and rearward in the horizontal direction, and a front end portion thereof is connected to the upper plate 16.

Further, the sample injecting apparatus 100' is provided with a frame member 101 movable on the floor face 2, and the frame member 101 is installed with a sample tank 102 containing the sample, arranged with a liquid feeding pump 103 thereabove, and installed with a switch valve 104 and a flow meter 105 further thereabove. Further, a pipe 106 extended upward from the sample tank 102 is connected to a suction side of the liquid feeding pump 103, and a pipe 107 extended from a delivery side of the liquid feeding pump 103 is connected to a sample injecting connector 17 connected to the lower bearing portion 50 of the rotating apparatus portion 10. Further, a pipe 108 is extended to direct to the sample injecting apparatus 100' from a sample discharging connector 18 connected to an upper end of the drive portion 30, and an end portion thereof is inserted into the sample discharging tank, not illustrated.

Further, the control apparatus portion 200 is constituted by installing a control panel 202 at an upper portion of a case 201 in a shape of a rectangular box, and although not illustrated, inside of the case 201 is integrated with a drive portion power source, a refrigerator for cooling water and the rotor 13, a vacuum pump for vacuuming a rotor chamber, not illustrated, at inside of the chamber 12, an oil pump for supplying oil to respective portions of the rotating apparatus portion 10, a hydraulic unit for driving the vertical lifts 70 and the horizontal lifts 80 and the like. Further, at the control panel 202, rotational number, operating time, temperature and the like of the rotor 13 can be set and displayed, and a switch for starting and stopping the apparatus is provided thereto.

Further, according to the centrifugal separator 1' having the above-described constitution, the sample in the sample tank 102 is injected into the rotor 13 from the sample injecting connector 17 of the rotating apparatus portion 10 by way of the pipes 106, 107 by the liquid feeding pump 103 of the sample injecting apparatus 100'. Further, the sample injected into the rotor 13 is centrifugally separated by rotating the rotor 13 at high speed, and the centrifugally separated sample (supernatant liquid or the like) is discharged from the sample discharging connector 18 to the sample discharging tank, not illustrated, by way of the pipe 108 as a discharge liquid, and the sample (separated sample) including particles sedimented in the rotor 13 is recovered by being discharged to a sample recovery tank, not illustrated, from a side of a lower portion of the rotor 13 by opening inside of the rotor 13 to the atmosphere after stopping to rotate the rotor 13.

Meanwhile, after centrifugally separating the sample as described above, the rotor 13 is taken out from the chamber 12 and is cleaned, or sterilized as necessary and thereafter, the rotor 13 is integrated into the chamber 12, since the rotor 13 is provided with a large weight, the rotor 13 is attached and detached by the vertical lift 70 and the horizontal lift 80 which are hydraulically operated as follows.

That is, when the vertical lift 70 is driven by hydraulic pressure supplied from the hydraulic unit, not illustrated, of the control apparatus portion 200, the horizontal lift 80 and the upper plate 16 attached at a front end portion thereof are moved upward along with the drive portion 30 and the rotor 13 to be lifted to a position indicated by a chain line in FIG. 15. Further, when the horizontal lift 80 is driven hydraulically to move forward from the position, the upper plate 16 supported by the front end portion is moved forward to an escaping position indicated by a chain line in FIG. 15 along with the drive portion 30 and the rotor 13 and therefore, the rotor 13 is taken out from the chamber 12 thereby. Further, the rotor 13 taken out from the chamber 12 is cleaned or further sterilized and thereafter, integrated into the chamber 12 by a procedure inverse to the above-described to be subjected to centrifugal separation again. Further, attachment and detachment of the rotor 13 by the hydraulic unit is described in Patent Reference 1, and a sterilizing processing by vapor is described in Patent Reference 2.

[Patent Reference 1] JP-A-2000-024551
[Patent Reference 2] JP-A-2000-042449

SUMMARY OF THE INVENTION

Meanwhile, when the sample to be separated centrifugally is, for example, influenza virus, Japanese encephalitis virus or the like, close attention is to be paid to handling thereof such that the sample is not contaminated by mixing other virus or bacteria, or an impurity or the like.

However, according to the centrifugal separating apparatus 1' of the background art shown in FIG. 14 and FIG. 15, there is needed an operation of taking out the rotor 13 from the chamber 12, disassembling and sterilizing the rotor 13, thereafter, integrating the sterilized rotor 13 again to integrate into the chamber 12 and thereafter, connecting the pipe 108 to the rotor 13 and therefore, in the operation, there is a possibility of mixing bacteria or the like floating in the atmosphere to a path of the sample (hereinafter, referred to as 'sample line'), sterilizing cannot be carried out in a state of integrating the rotor 13 and therefore, it is difficult to centrifugally separate the sample in a state of maintaining a sterile state.

Further, also the sample injecting apparatus 100' is disintegrated and thereafter integrated after sterilizing parts forming the sample line and the parts are connected to the rotating apparatus portion 10 and therefore, it is very difficult to completely maintain a sterile state.

The invention has been carried out in view of the above-described problem, and it is an object thereof to provide a centrifugal separator capable of realizing to centrifugally separate a sample under a complete sterile state by sterilizing a portion thereof with which at least the sample is brought into contact in a state of integrating a rotor.

In order to achieve the above-described object, the invention provides a centrifugal separator for centrifugally separating a sample by supplying the sample from a sample line into a rotor of a rotating apparatus portion and driving to rotate the rotor in a rotor chamber and discharging the centrifugally separated sample from the rotor via the sample line. The centrifugal separator includes a sterilizing apparatus for sterilizing at least a portion with which the sample is brought into contact by making a sterilizing fluid flow through the sample line.

BRIEF DESCRIPTION OF THE DRAWINGS

The present invention may be more readily described with reference to the accompanying drawings.

DETAILED DESCRIPTION OF THE PREFERRED EMBODIMENTS

An embodiment of the invention will be explained in reference to the attached drawings as follows.

Embodiment 1

Figure 1:
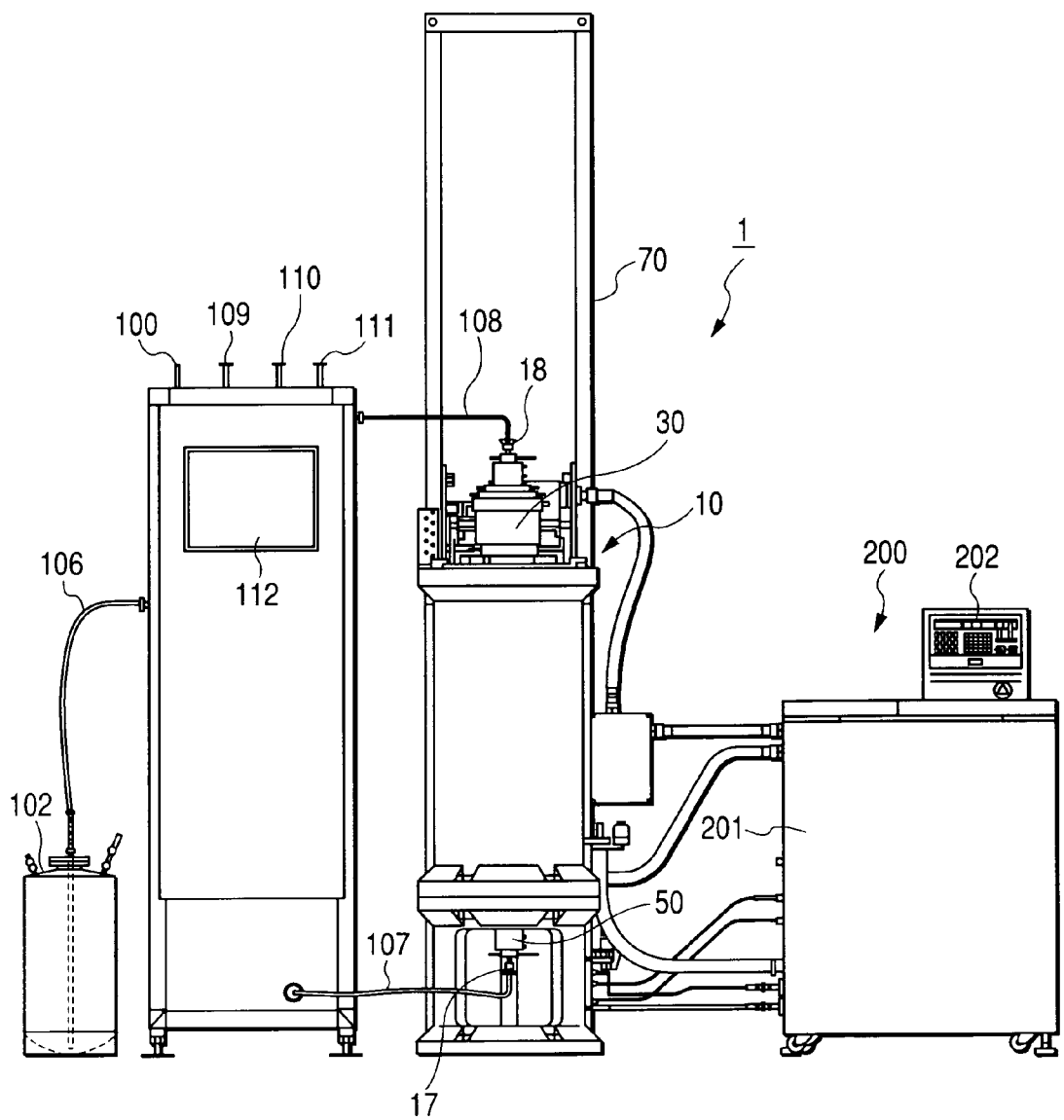
FIG. 1 is a front view of a centrifugal separator according to Embodiment 1 of the invention.

FIG. 1 is a front view of a centrifugal separator according to Embodiment 1 of the invention.

Figure 14:
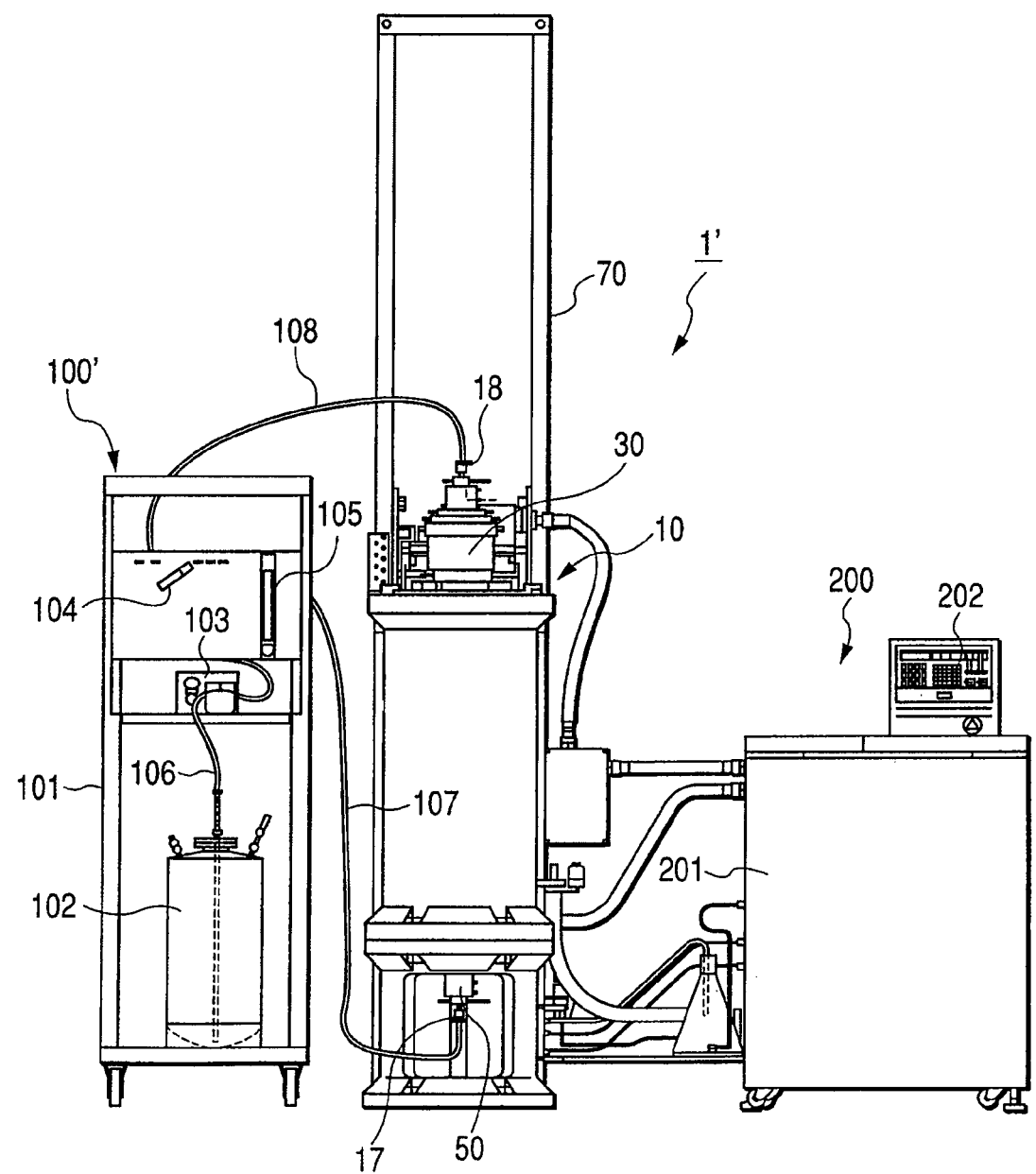
FIG. 14 is a front view of a centrifugal separator of a background art.
Figure 15:
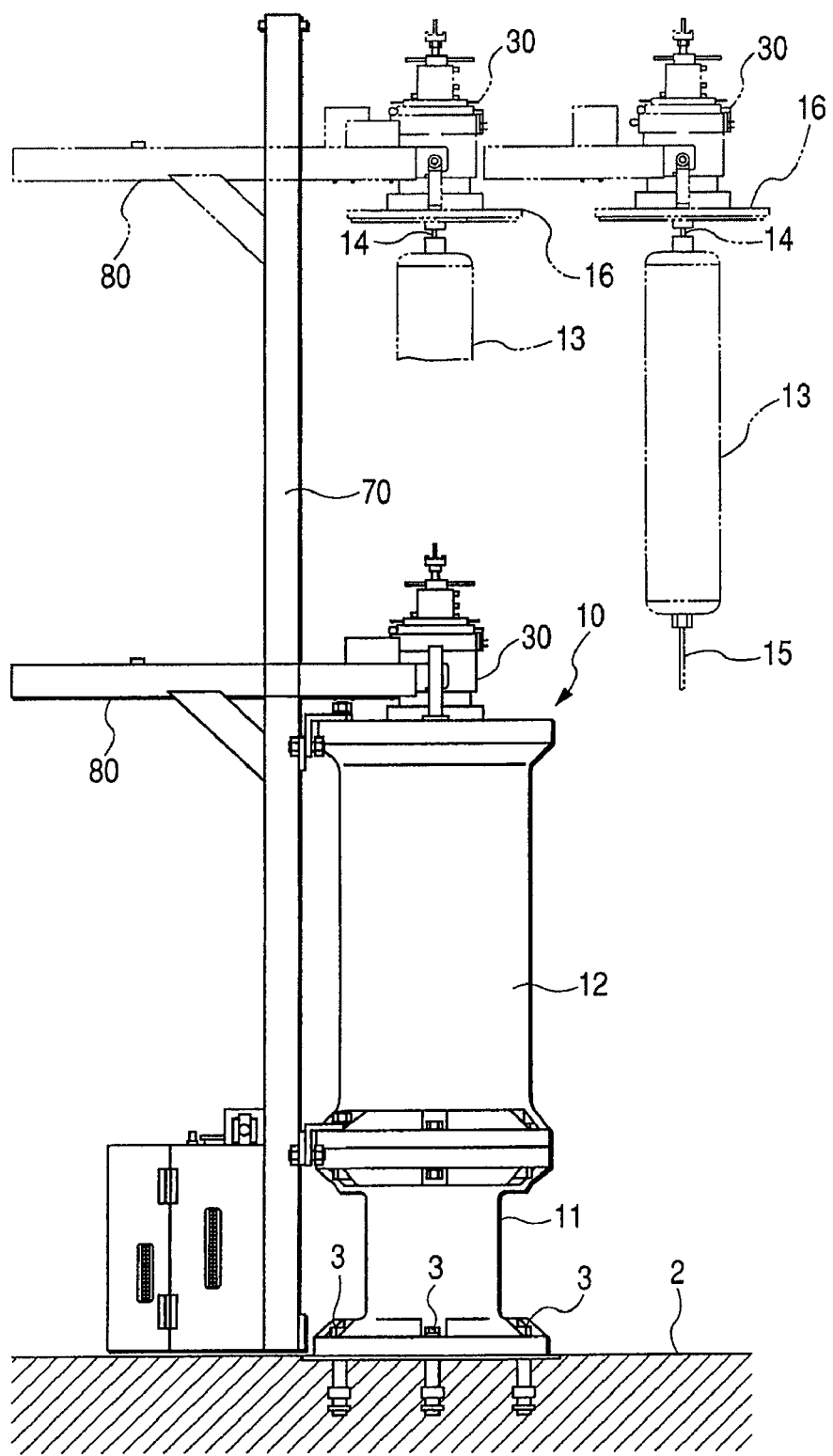
FIG. 15 is a side view showing operation of attaching and detaching a rotor in the centrifugal separator of the background art.

Although first, a total constitution of a centrifugal separator 1 according to the invention will be explained in reference to FIG. 1, the centrifugal separator 1 according to the invention is constructed by a constitution similar to that of the centrifugal separator 1' of the background art except that a vapor sterilizing apparatus 100 is constituted by integrating sterilizing means to the sample injecting apparatus 100' of the centrifugal separator 1' of the background art shown in FIG. 14 and FIG. 15 and therefore, in FIG. 1, elements the same as those shown in FIG. 14 and FIG. 15 are attached with the same notations and hereinafter, an explanation thereof at a second time will be omitted.

The vapor sterilizing apparatus 100 shown in FIG. 1 is constituted independently from the rotating apparatus portion 10 and the control apparatus portion 200 for controlling the rotating apparatus portion 10, inside thereof is constituted by integrating the liquid feeding pump 103 (refer to FIG. 5) shown in FIG. 14 and a control portion, not illustrated, other than various pipes (refer to FIG. 5), mentioned later, and an upper portion thereof is respectively erected with a vapor connecting port 109, a distilled water connecting port 110 and an air connecting port 111.

Further, an operation panel 112 is provided at an upper portion of a front face of the vapor sterilizing apparatus 100, an operator can set various kinds of operation by the operation panel 112, and a control portion of the vapor sterilizing apparatus 100 controls an air drive valve and an electric valve in accordance with settings (conditions) inputted from the operation panel 112. Further, numeral 102 designates the sample tank constituted by containing a sample to be centrifugally separated at inside thereof, the pipe 106 extended upward from the upper portion is connected to a suction side of the liquid feeding pump 103 (refer to FIG. 5) integrated to inside of the vapor sterilizing apparatus 100, and the pipe 107 conducted from the delivery side of the liquid feeding pump 103 is connected to the sample injecting connector 17 provided at a lower portion of the rotating apparatus portion 10. Further, the pipe 108 conducted from the sample discharging connector 18 provided at the upper portion of the drive portion 30 of the rotating apparatus portion 10 is connected to a side portion of the vapor sterilizing apparatus 100 and is inserted into a sample discharge tank, not illustrated, provided in the vapor sterilizing apparatus 100.

Figure 3:
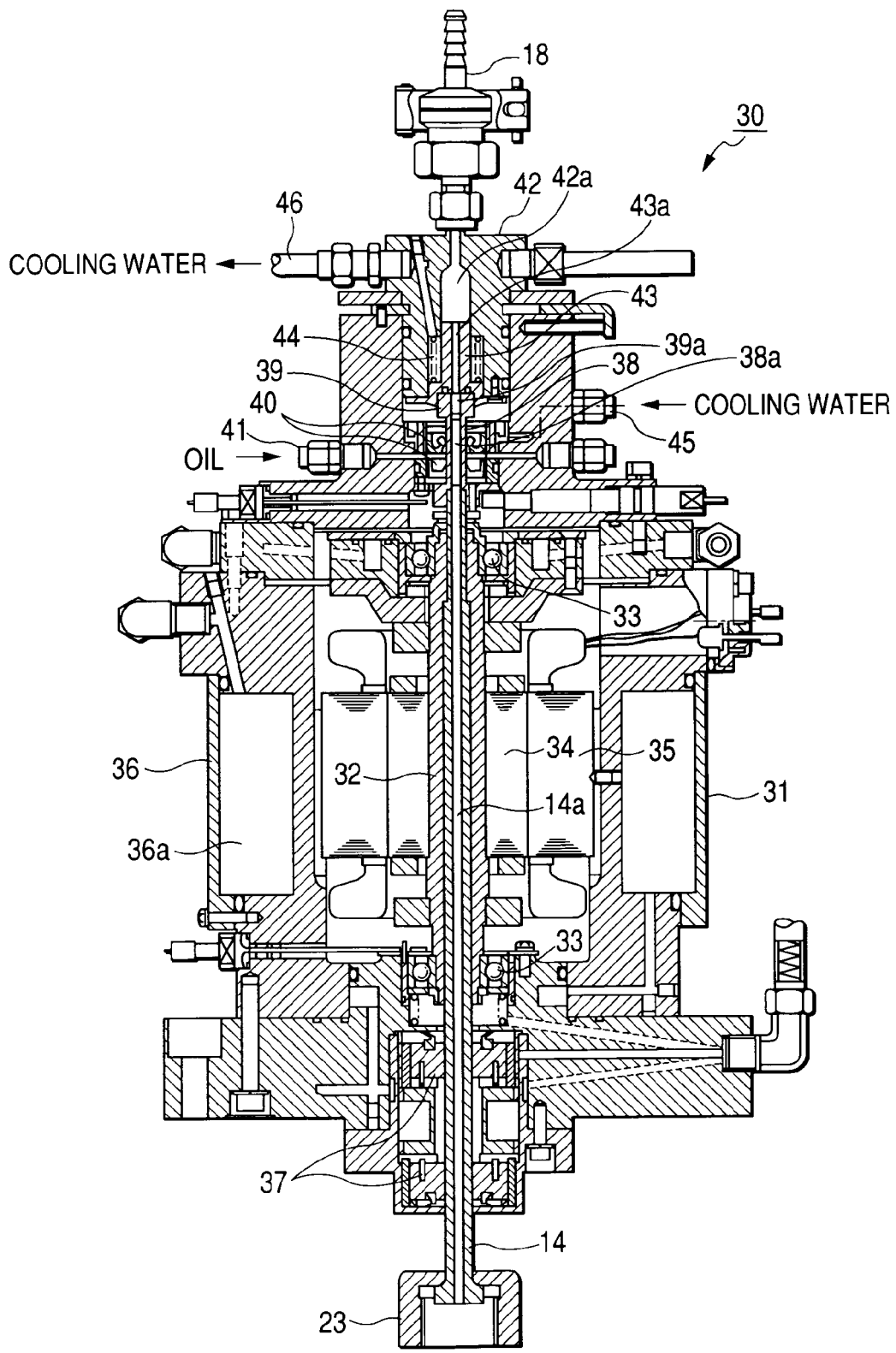
FIG. 3 is a vertical sectional view of a drive portion of the rotating apparatus portion of the centrifugal separator according to Embodiment 1 of the invention.
Figure 4:
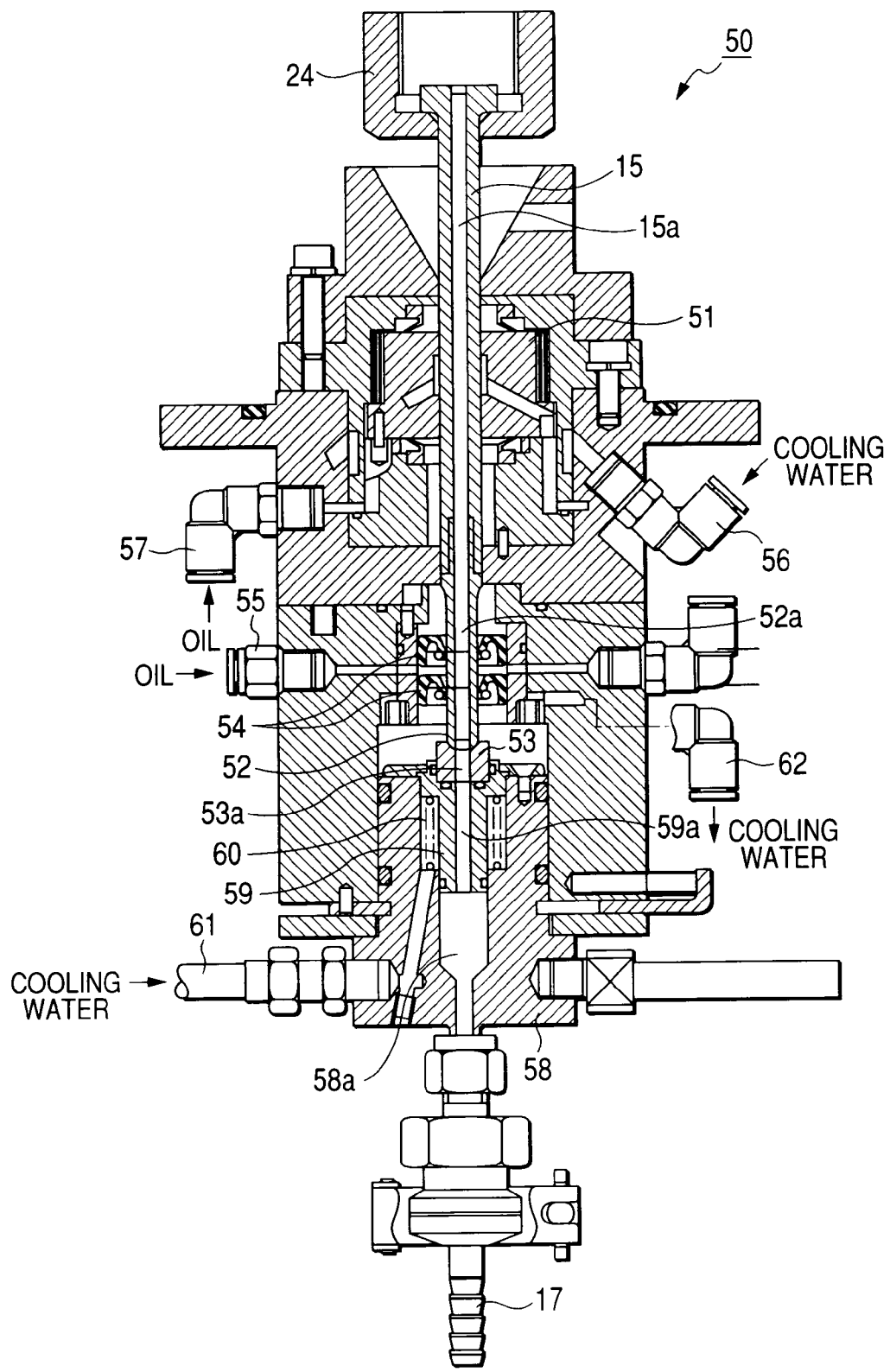
FIG. 4 is a vertical sectional view of a lower bearing portion of the centrifugal separator according to Embodiment 1 of the invention.

Next, details of the constitution of the rotating apparatus portion 10 will be explained in reference to FIG. 2 through FIG. 4. Further, FIG. 2 is a vertical sectional view breaking to show a portion of the rotating apparatus portion, FIG. 3 is a vertical sectional view of a drive portion of the rotating apparatus portion, and FIG. 4 is a vertical sectional view of the lower bearing portion of the rotating apparatus portion.

Figure 2:
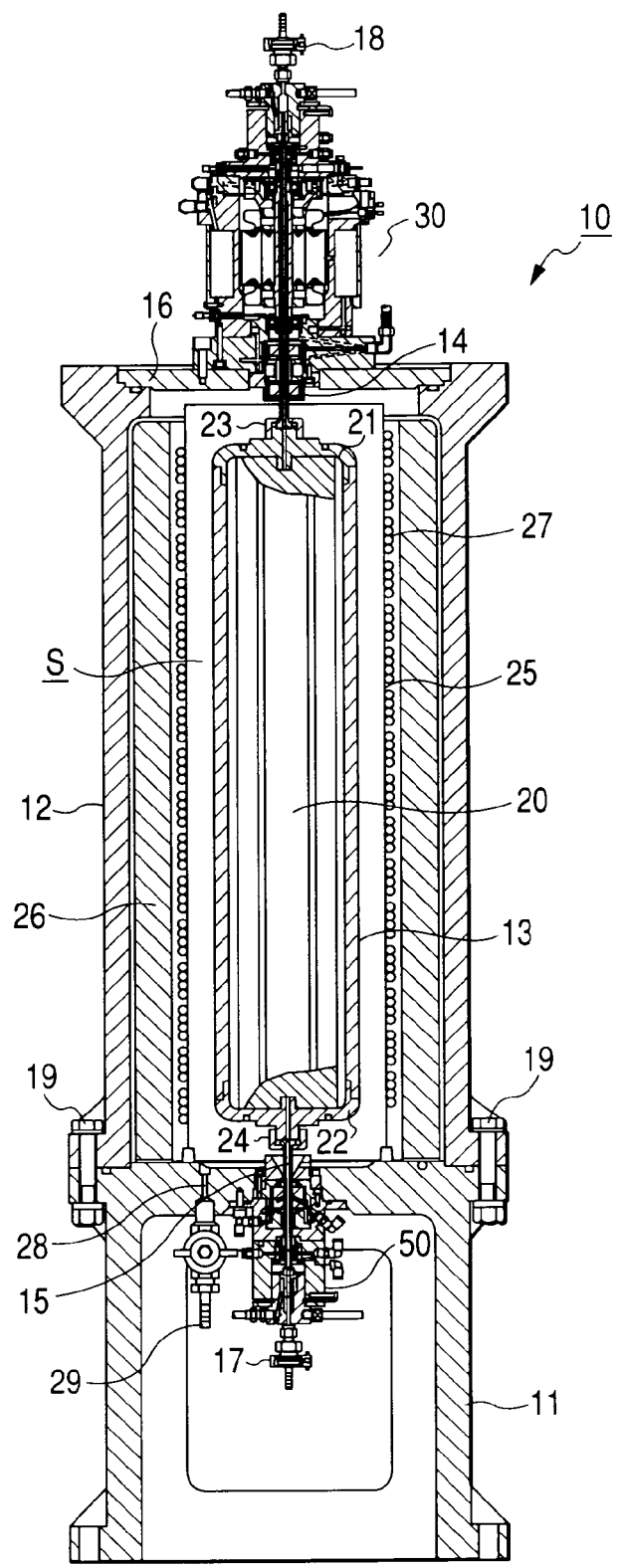
FIG. 2 is a vertical sectional view breaking to show a portion of a rotating apparatus portion of the centrifugal separator according to Embodiment 1 of the invention.

As shown by FIG. 2, a lower end flange portion of the chamber 12 of the rotating apparatus portion 10 is attached to the upper portion of the base 11 by a plurality of bolts 19, and the rotor 13 in a shape of a circular cylinder is vertically contained rotatably at an axis center portion at inside thereof. Here, a core 20 in a cylindrical shape is concentrically contained at inside of the rotor 13, and covers 21, 22 in a bowl-like shape are attachably and detachably screwed to upper and lower opening ends of the rotor 13. Further, center portions of the upper and the lower covers 21, 22 are attachably and detachably attached with the upper rotating shaft 14 and the lower rotating shaft 15 in a hollow shape respectively by rotor nuts 23, 24, the upper rotating shaft 14 and the lower rotating shaft 15 are respectively extended upward vertically and downward vertically, the upper rotating shaft 14 is connected to the drive portion 30, mentioned later, and the lower rotating shaft 15 is rotatably supported by the lower bearing portion 50.

Meanwhile, an upper end opening portion of the chamber 12 is attachably and detachably covered by the upper plate 16 in the shape of the circular plate, inside of the chamber 12 is formed with a rotor chamber S hermetically sealed by a case 25 containing the rotor 13, and an outer peripheral side of the case 25 is concentrically arranged with a protector 26 in a cylindrical shape. Further, an outer peripheral face of the case 25 is wound with a cooling coil 27 as a vaporizing tube, and the rotor chamber S is deprived of latent heat to cool by an evaporating cold medium flowing in the cooling coil 27. Further, a bottom portion of the rotor chamber S is opened with a drain hole 28 penetrated through an upper wall of the base 11, and the drain hole 28 is connected with a connector 29. Further, the rotor chamber S is connected to a vacuum pump, not illustrated, provided at the control apparatus portion 200 shown in FIG. 1. Further, the cooling coil 27 is supplied with the cold medium from a refrigerator, not illustrated, for cooling the rotor provided at the control apparatus portion 200, and the cold medium is circulated in a cold medium pipe of a closed loop including the cooling coil 27 to repeat cooling operation.

Further, the drive portion 30 for driving to rotate the rotor 13 at high speed is installed above the upper plate 16 and a detailed constitution of the drive portion 30 will be explained in reference to FIG. 3.

The drive portion 30 includes an electric motor 31 as a drive source, an output shaft 32 in a hollow shape of the electric motor 31 is vertically arranged, and upper and lower portions thereof are rotatably supported by a pair of ball bearings 33. Here, the electric motor 31 is constituted by fixedly providing a stator 35 at a surrounding of a rotor 34 rotated along with the output shaft 32, and a cooling water jacket 36a is formed at a motor housing 36 for containing these. Therefore, the electric motor 31 is cooled by cooling water flowing in the cooling water jacket 36a to restrain heat generation thereof. Further, the cooling water is supplied from the refrigerator, not illustrated, provided at the control apparatus portion 200.

Further, the output shaft 32 of the electric motor 31 is inserted to fixedly attach with the upper rotating shaft 14, and a lower end portion thereof extended downward from the output shaft 32 of the upper rotating shaft 14 is rotatably supported by a pair of upper and lower sliding bearings 37.

Further, an upper end portion projected upward from the output shaft 32 of the upper rotating shaft 14 is screwed with a shaft head 38 in a cylindrical shape and an upper end portion of the shaft head 38 is brought into contact with a mechanical seal 39 constituted by low sliding plastic having heat resistance. Further, an outer peripheral face of the shaft head 38 is sealed by a pair of upper and lower lip seals 40, and the lip seals 40 are lubricated by oil supplied from an oil injecting port 41.

Further, the mechanical seal 39 is held movably in an up and down direction by a seal holder 43 held slidably in an up and down direction by a seal connector 42, both members are urged downward by a spring 44 and therefore, the mechanical seal 39 is brought into contact with an upper end of the shaft head 38 by predetermined pressure. Further, the mechanical seal 39 is cooled by cooling water supplied from a cooling water inlet 45 and cooling water the temperature of which rises by being subjected to cooling is discharged from a cooling water outlet 46.

Meanwhile, oil is supplied to the ball bearing 33 and the sliding bearing 37 other than the lip seal 40, the oil is supplied from an oil pump, not illustrated, provided at the control apparatus portion 200 and is circulated in an oil pipe, not illustrated, constituting a closed loop to be subjected to lubrication of respective portions. Further, cooling water for cooling the electric motor 31 and the lip seal 40 is supplied from the refrigerator, not illustrated, provided at the control apparatus portion 200 to be subjected to cooling of respective portions.

Further, a center portion of an upper portion of the seal connector 42 is attached with the sample discharging connector 18 and the sample discharging connector 18 is connected with the pipe 108 shown in FIG. 1.

Further, an axis center of the drive portion 30 constituted as described above is formed with a sample line (a portion of a line d shown in FIG. 5) by paths 42a, 43a, 39a, 38a, 14a in a shape of a circular hole penetrated through respective center portions of the seal connector 42, the seal holder 43, the mechanical seal 39, the shaft head 38 and the upper rotating shaft 14, a lower end of the sample line is communicated with an upper portion of inside of the rotor 13 and an upper end thereof is connected to the pipe 108 (refer to FIG. 1) via the sample discharging connector 18.

Next, details of the constitution of the lower bearing portion 50 will be explained in reference to FIG. 4.

The lower bearing portion 50 is for rotatably supporting the lower rotating shaft 15, the lower rotating shaft 15 is rotatably supported by a sliding bearing 51, and a lower end portion of a shaft head 52 screwed to a lower end portion thereof is brought into contact with a mechanical seal 53 constituted by low sliding plastic having heat resistance. Further, an outer peripheral face of the shaft head 52 is sealed by a pair of upper and lower lip seals 54, and the lip seals 54 are lubricated by oil supplied from an oil injecting port 55. Further, the sliding bearing 51 is cooled by cooling water supplied from a cooling water inlet 56 and is lubricated by oil supplied from an oil injecting port 57. Further, cooling water is supplied from the refrigerator, not illustrated, provided at the control apparatus portion 200.

Further, the mechanical seal 53 is held movably in an up and down direction by a seal holder 59 held slidably in an up and down direction by a seal connector 58, both members are urged upward by a spring 60 and therefore, the mechanical seal 53 is brought into contact with a lower end of the shaft head 52 by predetermined pressure. Further, the mechanical seal 53 is cooled by cooling water supplied from a cooling water inlet 61 and cooling water the temperature of which rises by being subjected to cooling is discharged from a cooling water outlet 62.

Meanwhile, oil supplied to the lip seal 54 and the sliding bearing 51 is supplied from the oil pump, not illustrated, provided at the control apparatus portion 200 and is circulated through an oil pipe constituting a closed loop to be subjected to lubrication of respective portions. Further, cooling water for cooling the lip seal 54 is supplied from the refrigerator, not illustrated, provided at the control apparatus portion 200 to be subjected to cooling of the lip seal 54.

Further, the sample injecting connector 17 is attached to a center portion of a lower portion of the seal connector 58 and the sample injecting connector 17 is connected with the pipe 107 shown in FIG. 1.

Further, an axis center of the lower bearing portion 50 constituted as described above is formed with a sample line (a portion of the line d shown in FIG. 5) in an up and down direction by paths 58a, 59a, 53a, 52a, 15a in a shape of a circular hole penetrated through respective center portions of the seal connector 58, the seal holder 59, the mechanical seal 53, the shaft head 52 and the lower rotating shaft 15, an upper end of the sample line is communicated with a lower portion of inside of the rotor 13, and a lower end thereof is connected to the pipe 107 (refer to FIG. 1) via the sample injecting connector 17.

Next, a piping constitution of the vapor sterilizing apparatus 100 will be explained in reference to FIG. 5.

Figure 5:
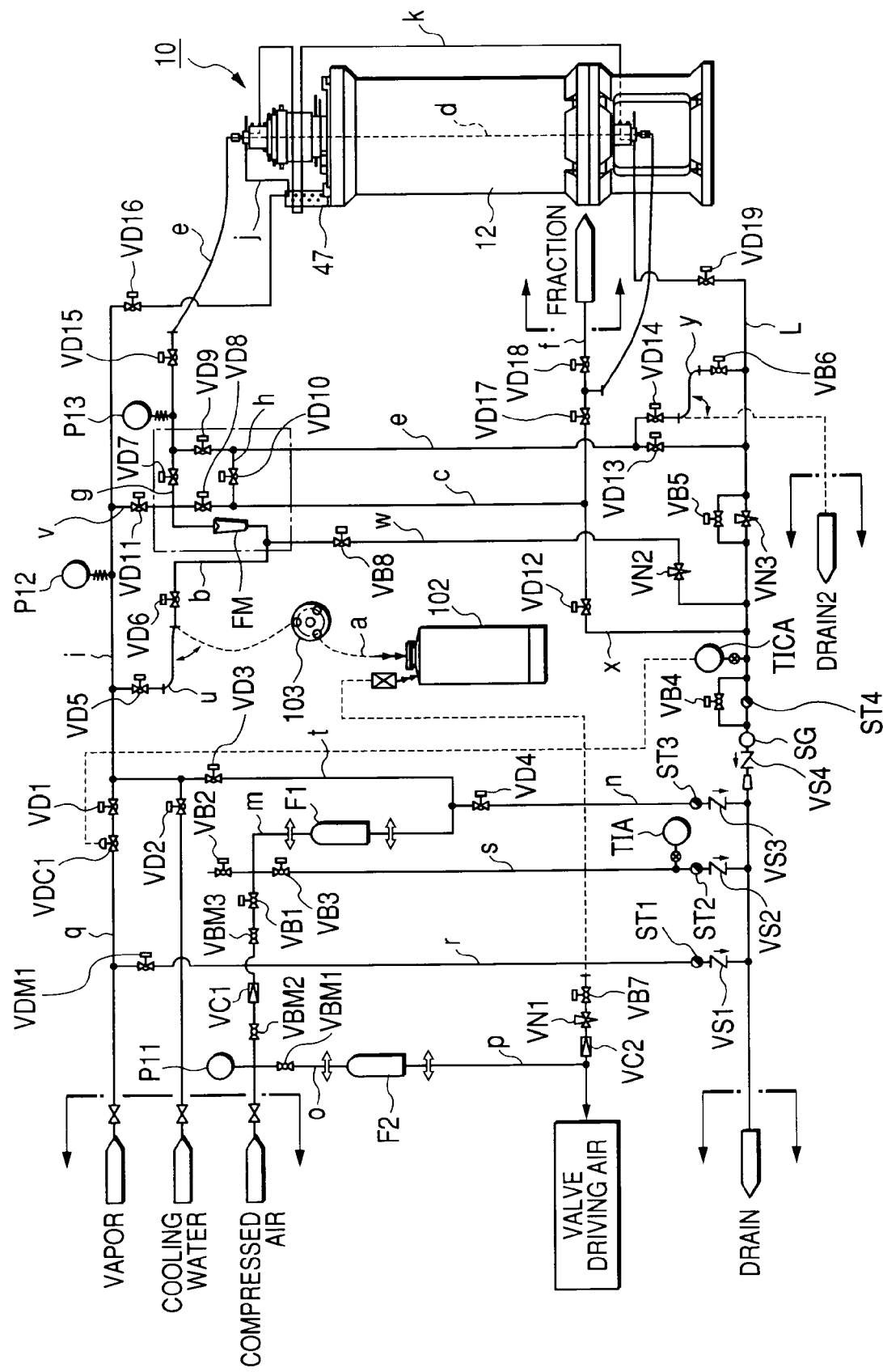
FIG. 5 is a piping diagram of the vapor sterilizing apparatus of the centrifugal separator according to Embodiment 1 of the invention.

FIG. 5 is a piping diagram of the vapor sterilizing apparatus 100, and pipings of the vapor sterilizing apparatus 100 are constituted by including existing sample line, cooling water line and air line.

That is, in FIG. 5, the sample line is constituted by including a line a reaching the liquid feeding pump 103 from the sample tank 102 (pipe 106 shown in FIG. 1), a line b reaching a flow meter FM from the liquid feeding pump 103 via a valve VD 6, a line c reaching the lower portion of the chamber 12 of the rotating apparatus portion 10 from the flow meter FM via valves VD8 and VD17, the line d formed in the chamber 12, a line e reaching a sample discharged tank (DRAIN2), not illustrated, from the upper portion of the drive portion 30 via a valve VD15, a pressure gauge P13, valves VD9 and VD14, and a line f reaching a sample recovery tank (FRACTION), not illustrated, by being branched from a downstream side of the valve VD17 of the line c by way of a valve VD18. Further, the line c and the line e are respectively connected by lines g, h by interposing the valves VD8 and VD9, the lines g, h are respectively provided with valves VD7, VD10.

Further, the cooling water line is a line for making cooling water of distilled water or the like (for example, ultra pure water (UFW)) from a distilling facility, not illustrated, and is constitute by including a line i reaching a connecting portion 47 at the upper portion of the chamber 12 from the distilling facility via a valve VD2, a pressure gauge P12 and a valve VD16, a line j reaching the drive portion 30 from the connecting portion 47, a line k reaching the lower bearing portion 50 from the drive portion 30, and a line L reaching drain (DRAIN) from the lower bearing portion 50 via valves VD19, VB5 (or VN3), a thermometer TICA, a valve VB4 (or steam trap ST4), a sight glass SG and a check valve VS4. Further, according to the embodiment, distilled water at 4° C. is used as the cooling water.

Further, the air line is a line for making air for blowing or for driving a valve flow from a compressed air supplying facility of an air compressor or the like, not illustrated, and is constituted by including a line m reaching a filter F1 from the compressed air supplying facility, not illustrated, via a pressure gauge Pl1, valves VBM2, VC1, VBM3 and VB1, a line n connected to the line L from the filter F1 via a valve VD4, a steam trap ST3 and a check valve VS3, a line o reaching a filter F2 via a valve VBM1 by being branched from an upstream side of the valve VBM2 of the line m, and a line p conducted from the filter F2.

Further, the vapor sterilizing apparatus 100 according to the embodiment adopts a piping constitution of adding a line for making steam (pure steam (PS)) as a sterilizing fluid flow to the sample line, the cooling water line and the air line, explained above.

That is, a line q extended from a steam generating apparatus, not illustrated, of a boiler or the like is connected between the valve VD2 and the pressure gauge P12 of the line i and a middle portion thereof is provided with valves VDC1 and VD1. Further, a line r branched from a middle of the line q is connected to the line L via a valve VDM1, a steam trap ST1 and a check valve VS1, a line s is branched from between the valve VB1 and the filter F1 of the line m, one end of the line s is opened to the atmosphere via a valve VB2, and other end thereof is connected to the line L via a valve VB3, a thermometer T1A, a steam trap ST2 and a check valve VS2.

Further, a line t branched from between the valve VD2 and the pressure gauge P12 of the line i is connected between the filter F1 and the valve VD4 of the line n via a valve VD3, a line u branched from between the valve VD1 and the pressure gauge P12 of the line q is connected between the liquid feeding pump 103 and the valve VD6 of the line b via a valve VD5, and a line v branched from between the pressure gauge P12 and the valve VD16 is connected between the flow meter FM and the valve VD8 via a valve VD11.

Further, a line w branched from between the valve VD6 and the flow meter FM of the line b is connected to the line L via valves VB8 and VN2, and a line x branched from between the valves VD8 and VD17 of the line c is connected to the line L via a valve VD12, and a line y branched from between the valves VD9 and VD13 of the line e is connected to the line L via valves VD14 and VB6.

Further, in the above-described, the valves VBM1 through VBM3 are manual ball valves, the valves VB1 through VB7 are air driven ball valves, the valve VDM1 is a manual diaphragm valve, the valves VD1 through VD19 are air driven diaphragm valves, the valve VDC1 is a diaphragm control valve, the valves VC1, VC2 are pressure reducing valves and the valves VN1 through VN3 are needle valves.

Next, a series of operation of centrifugal separation by the centrifugal separator 1 according to the invention will be explained in an order of steps in reference to FIG. 6 through FIG. 11, and the operation is executed by being processed by 1) vapor sterilizing step, 2) air blowing and rotor cooling step, 3) centrifugally separating step, 4) air blowing step, 5) separated sample recovering step and 6) cleaning step. Further, FIG. 6 through FIG. 11 are piping diagrams similar to FIG. 5 showing flows of various fluids (steam, cooling water and air) and elements in the drawings, elements the same as those in FIG. 5 are attached with the same notations.

Figure 6:
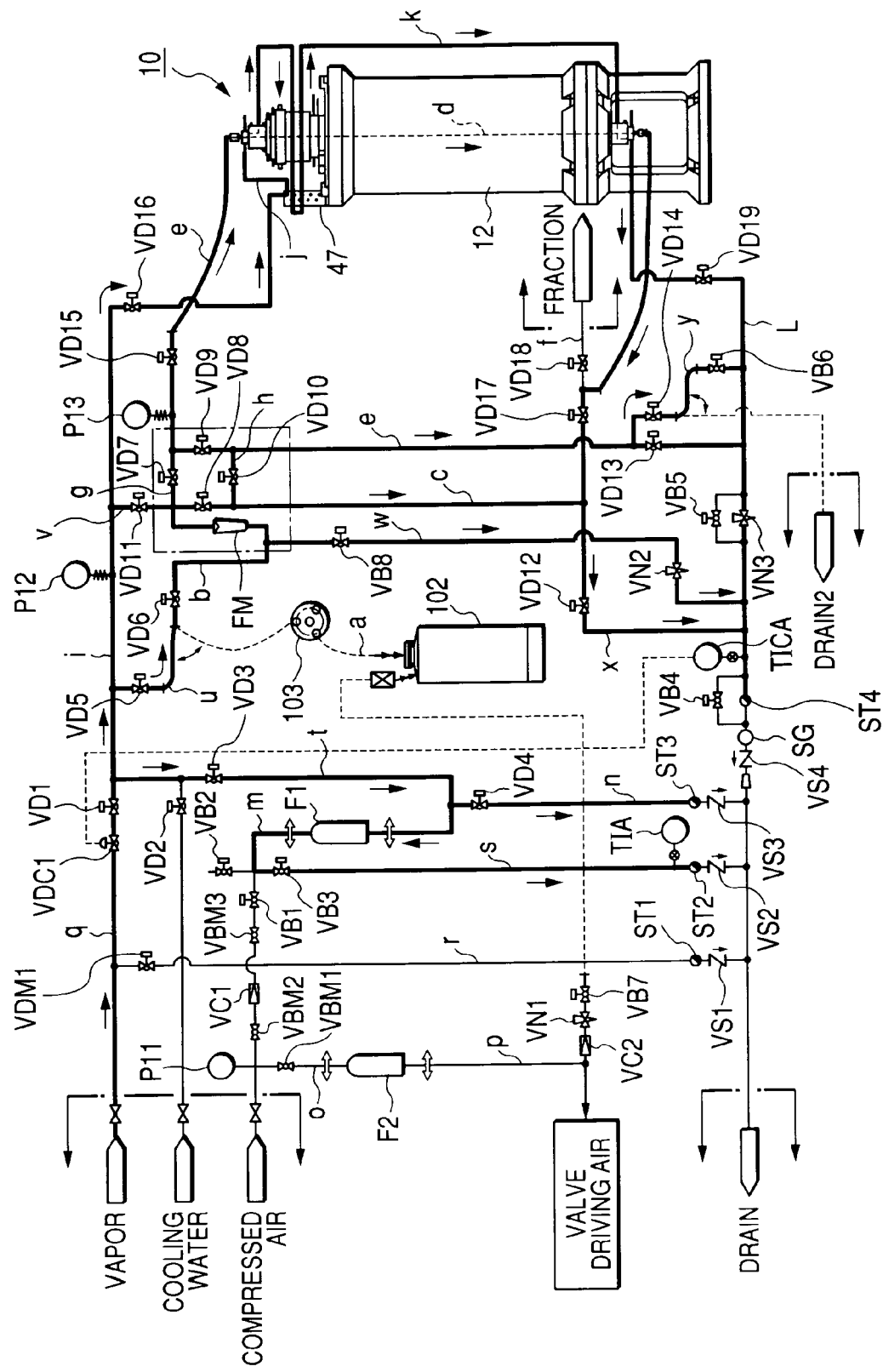
FIG. 6 is a piping diagram showing flow of vapor at a vapor sterilizing step in the centrifugal separator according to Embodiment 1 of the invention.

1) Vapor Sterilizing Step:

The vapor sterilizing step is a step which is carried out after finishing centrifugally separating operation at a preceding time, taking out the rotor 13 from the chamber 12 to subject to disassembling, cleaning and sterilizing processings, integrating the rotor 13 subjected to the processings to integrate into the chamber 12, connecting the pipe 107 to the sample injecting connector 17 of the lower bearing portion 50, and connecting the pipe 108 to the sample discharging connector 18 of the drive portion 30, and in the step, steam (PS) at high temperature is made to flow via paths indicated by arrow marks in FIG. 6. Here, steam temperature in the pipe is measured by the thermometer TICA, and the steam temperature in the pipe is controlled by controlling the valve VDC1 such that the temperature falls in a range of 121° C. through 130° C., and controlling a flow rate of steam flowing in the pipe and a pressure in the pipe. Thereby, at least a portion with which the sample is brought into contact is sterilized by vapor.

That is, steam supplied from the steam generating facility of a boiler or the like flows in the line q and a portion thereof flows to the lines t, n, m, s to sterilize the lines. Further, water drops liquefied by being cooled in the midst are discharged from the steam traps ST2, ST3.

Further, other steam is made to flow to a side of the line i which is a cooling water line and a portion thereof is made to flow to a side of the line u constituting a side of the sample line. Further, a portion of steam flowing to the side of the line u is branched at the line e via the lines b, g and flows in the line d formed in the chamber 12 via the sample discharging connector 18 provided at the upper portion of the chamber 12 and reaches the line L via the lines c, x as shown by arrow marks in the drawing. Meanwhile, a portion of steam branched at the line e merges steam flowing in the line c via the line h and a remaining portion thereof is branched to a side of the valve VD13 of the line e and the line y to reach the line L. Further, a portion of steam flowing in the line b passes through the line w to reach the line L. Further, the valve VN2 is arranged at the line w to reduce a flow rate of steam flowing in the line w having a small resistance to make steam flow to sides of the lines c, e, d, k. In the line L, water drops of steam liquefied by being cooled at a middle thereof are discharged to the drain (DRAIN) via the steam trap ST4 and the check valve VS4.

On the other hand, a portion of steam flowing from the line q to the side of the line i merges steam flowing in the line b via the line v and other steam flows in the lines j, k constituting the cooling water lines in illustrated arrow mark directions to reach the line L. Further, water drops liquefied by being cooled at a middle thereof are discharged to the steam trap ST4. Further, the valve VN3 is arranged at the line L for reducing a flow rate of steam flowing in the lines e, k having small resistances and making steam flow to the sides of the lines c, d similar to the above-described.

Meanwhile, the above-described sterilizing processing is carried out in a state of maintaining inside of the rotor chamber S in the chamber 12 in a vacuum state by driving the vacuum pump, not illustrated, provided at the control apparatus portion 200. When inside of the rotor chamber S is maintained in the vacuum state, the rotor chamber S forms a thermally insulating layer to reduce transfer of heat and therefore, the rotor 13 is heated by steam at an early stage, the rotor 13 is sterilized efficiently, and the chamber 12 is not brought under high temperature, which is safe. Further, the shaft heads 38, 52 and the lip seals 40, 54 are respectively brought into close contact with each other and therefore, there is also achieved an effect of firmly preventing invasion of steam.

Further, during the sterilizing processing, oil is supplied to the lip seals 40, 54, ball bearing 33 and the sliding bearings 37, 51 of the drive portion 30 shown in FIG. 3 of the rotating apparatus portion 10. By making oil flow to the lip seals 40, 54, the shaft heads 38, 52 and the lip seals 40, 54 are respectively brought into close contact with each other and invasion of steam is prevented by preventing deformation of lip portions of the lip seals 40, 54 by vapor pressure. As a result, leakage of steam from the parts and invasion of the atmosphere are firmly prevented by a seal effect by oil and sterilizing can firmly be carried out. Further, the ball bearing 33, inside of the electric motor 31, the sliding bearings 37, 51 and the like can be prevented from being rusted (corroded) by moisture of steam.

Figure 7:
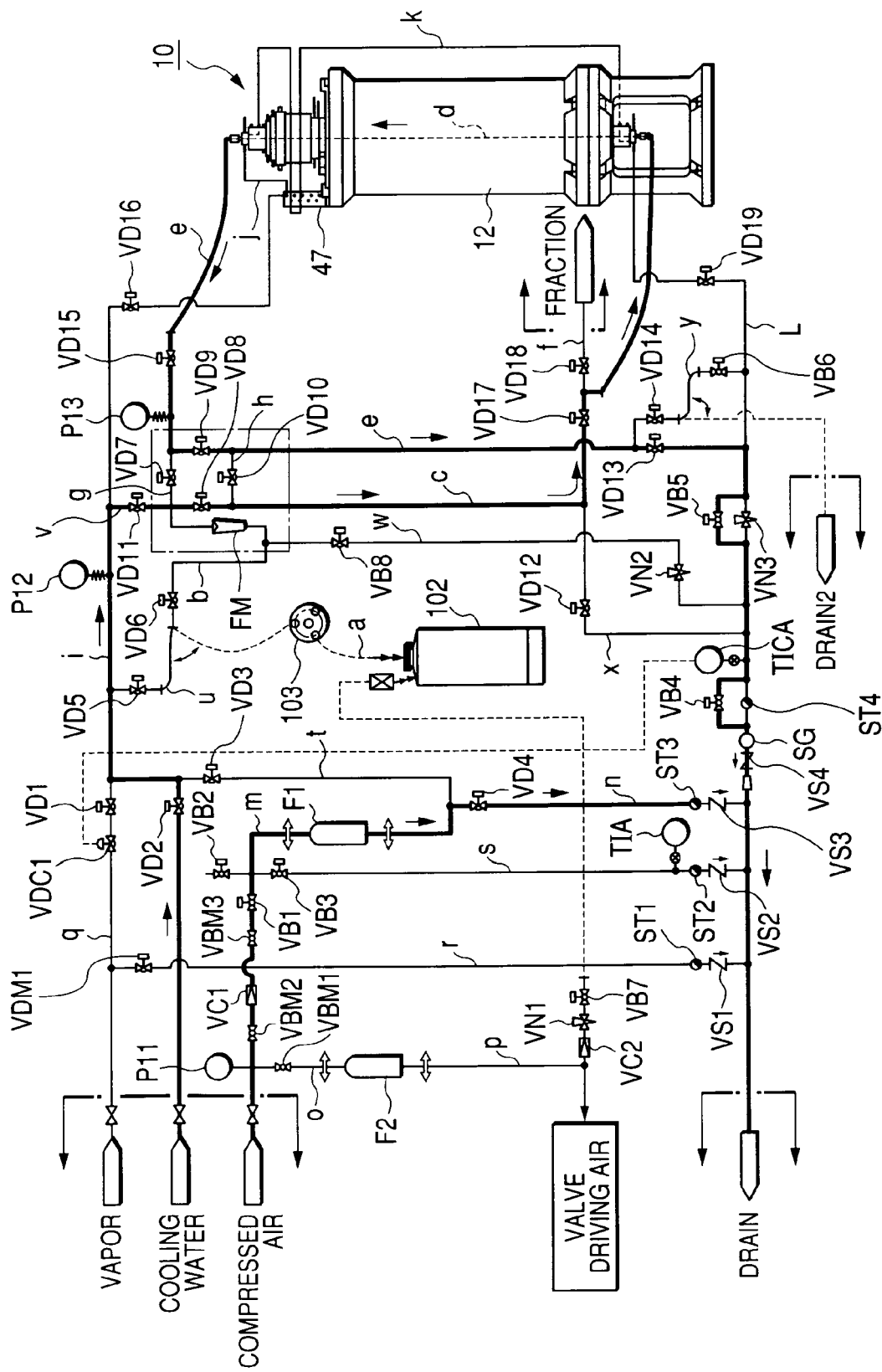
FIG. 7 is a piping diagram showing flow of air and cooling water at an air blowing and rotor cooling step in the centrifugal separator according to Embodiment 1 of the invention.

2) Air Blowing and Rotor Cooling Step:

When the vapor sterilizing step has been finished, the operation proceed to the successive air blow and rotor cooling step, in the step, as shown by arrow marks in FIG. 7, compressed air from a compressed air supplying facility of an air compressor or the like is made to flow to the filter F1 via the line m and therefore, the filter F1 is dried by air, and air subjected to drying of the filter F1 is made to flow in the line n in an illustrated arrow mark direction and is discharged to the drain (DRAIN) by passing the check valve VS3 from the steam trap ST3.

Further, cooling water from a distilling facility, not illustrated, is made to flow in the line i constituting the cooling water line in an illustrated arrow mark direction, and is made to flow to the line v which is the sample line from the line i. Further, cooling water which is made to flow to the line v cools the rotor 13 from inside thereof in a procedure of flowing upward in the line d at inside of the chamber 12 by passing the line c and thereafter flows to the line L by passing the line e and is discharged to the drain (DRAIN). Thereafter, the valve VD2 is closed and the valve VD3 is opened and air is blown for removing moisture in the steam pipe to dry.

In this way, when the rotor 13 which is brought under high temperature by being heated by steam in the vapor sterilizing step as the preceding step is cooled by cooling water, centrifugal separating operation of the sample at the successive centrifugally separating step can swiftly be carried out.

Further, when the centrifugally operating processing is not carried out immediately after finishing the vapor sterilizing step, the air blow and rotor cooling step, by compressed air supplied from the compressed air supplying facility of an air compressor or the like, the sample line and the cooling water line are maintained in a state of being pressurized to a predetermined pressure (0.1 MPa according to the embodiment) by compressed air, and invasion of the atmosphere into the lines to be processed can be prevented. As a result, invasion of bacteria floating in the atmosphere to the lines to be processed can firmly be prevented.

Meanwhile, bidirectional communication can be carried out between the control portion (not illustrated) provided in the vapor sterilizing apparatus 100, and the control apparatus portion 200. The control portion controls to operate the vapor sterilizing apparatus 100 based on a signal from the control apparatus portion 200. For example, in order to confirm presence or absence of oil made to flow to the lip seal 40 to the drive portion 30 in the vapor sterilizing step, the control portion receives a signal from a sensor for detecting supply current (or supply voltage) to the motor for driving the oil pump or a signal from a flow rate meter arranged in the oil line, or receives a signal of a sensor for detecting a vacuumed state (reduced pressure state) in the chamber 12, and controls to operate the vapor sterilizing apparatus based on the signals.

Further, the control portion of the vapor sterilizing apparatus 100 can transmit a signal indicating a state of opening and closing the valves of the vapor sterilizing apparatus 100, or an operating state of temperatures in the pipes, flow rates of cooling water, compressed air, steam or the like to the control apparatus portion 200, the control portion and the control apparatus portion 200 can always confirm the states of operating the vapor sterilizing apparatus 100 and the rotating apparatus portion 10 to each other, and the vapor sterilizing apparatus 100 and the rotating apparatus portion 10 are provided with output terminals for transmitting and receiving signals.

Further, also by integrating the control portion of the vapor sterilizing apparatus 100 in the control apparatus portion 200, the states of operating the vapor sterilizing apparatus 100 and the rotating apparatus portion 10 can similarly be confirmed always by each other, and the centrifugal separator 1 can be made to constitute a safer and further highly reliable apparatus.

3) Centrifugally Separating Step:

When the portion with which at least the sample is brought into contact is sterilized by the vapor sterilizing step, and the filter F1 is dried and the rotor 13 heated by vapor is cooled by the air blowing and rotor cooling step, the sample is centrifugally separated by the centrifugally separating step.

Prior to centrifugal separation, the line u is switched to a line on a side of the liquid feeding pump 103 frontward from the valve VD6, and similarly, the line y is switched to a line on a side of the sample discharging tank (DRAIN 2), not illustrated, rearward from the valve VD14.

Figure 8:
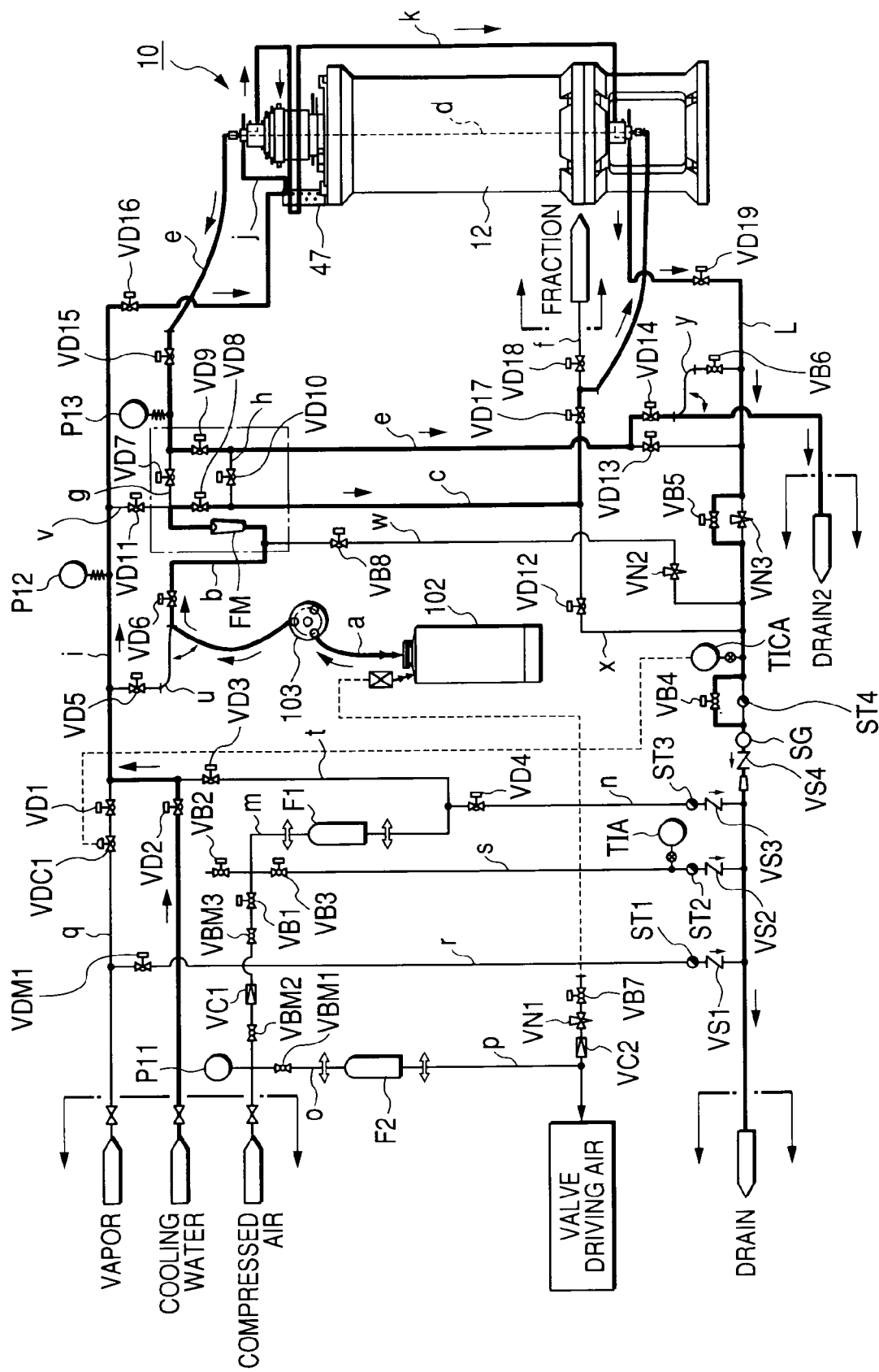
FIG. 8 is a piping diagram showing flow of a sample and cooling water in a centrifugally separating step in the centrifugal separator according to Embodiment 1 of the invention.

In the centrifugally separating step, as shown by arrow marks in FIG. 8, solutions are sucked from the line a from a plurality of tanks, not illustrated, containing solutions having different densities successively from solutions having small densities by the liquid feeding pump 103 and thereafter, delivered to the line b after elevating pressures thereof. Further, the solutions delivered to the line b are supplied from the line c into the chamber 12 from the lower portion and supplied to inside of the rotor 13 shown in FIG. 2 by passing the respective paths 58a, 59a, 53a, 52a, 15a formed in the seal connector 58, the seal holder 59, the mechanical seal 53, the shaft head 52 and the lower rotating shaft 15 of the lower bearing portion 50 shown in FIG. 4. When the solution having a density gradient is filled at inside of the rotor 13, the electric motor 31 of the drive portion 30 shown in FIG. 3 is driven, the rotation is transmitted to the rotor 13 via the output shaft 32 and the upper rotating shaft 14 and therefore, the rotor 13 is driven to rotate at high speed (for example, 40,000 rpm) at inside of the rotor chamber S brought into a vacuum state. Thereafter, the centrifugally separating processing is carried out by supplying the sample in the sample tank 102 from the sample injecting connector 17 at the lower portion of the chamber 12 into the rotor 13 by the liquid feeding pump 103 and recovering a sediment liquid from the sample discharging connector 18 at the upper portion of the chamber 12. Further, the sample may be supplied from the sample discharging connector 18 at the upper portion of the chamber 12 and the sediment liquid may be recovered from the connector 17 at the lower portion of the chamber 12. Further, although according to the embodiment, the sample in the sample tank 102 is sucked by the liquid feeding pump 103, there may be adopted a constitution of omitting the liquid feeding pump 103, supplying compressed air into the sample tank 102 and pressurizing the sample by pressure of compressed air.

Further, when the rotor 13 is rotated, inside of the rotor chamber S is brought into a vacuumed state and therefore, a resistance of air of the rotor 13 is restrained to be low to enable to rotate the rotor 13 at high speed and heat generation in accordance with rotation of the rotor 13 at high speed is restrained to be low. Further, the rotor chamber S is cooled by vaporizing the cold medium flowing in the cooling coil 27 wound around the outer peripheral face of the case 25 and centrifugally separating processing is carried out while the sample is being cooled.

Further, at the same time, cooling water flows in the lines i, j constituting the cooling water line from a distilling facility, not illustrated, first, cools the mechanical seal 39 of the drive portion 30 shown in FIG. 3, thereafter, flows in the line k and supplied to the lower bearing portion 50, and cools the mechanical seal 53 shown in FIG. 4. Further, cooling water the temperature of which rises by being subjected to cooling of respective portions is discharged to the drain (DRAIN) by passing the line L.

Further, when the rotor 13 is rotated at high speed in the rotor chamber S as described above, the sample filled at inside thereof is centrifugally separated, the centrifugally separated sample (sediment liquid or the like) is discharged to the sample discharge tank, not illustrated, from the sample discharging connector 18 via the pipe 108, and separated particles sediment in the rotor 13.

Meanwhile, in the vapor sterilizing step, in the state of integrating the rotor 13 to the chamber 12 and connecting the pipe 108 to the sample discharging connector 18, steam is made to flow through the sample line and the cooling water line to thereby sterilize the lines by the vapor sterilizing apparatus 100 and therefore, the sample can centrifugally be separated under the sterilized state. Further, particularly, also the cooling water line is sterilized by making vapor flow to the cooling water line and therefore, bacteria included in cooling water are firmly prevented from being mixed to the sample and centrifugal separation of the sample is realized under a further complete sterile state.

Figure 9:
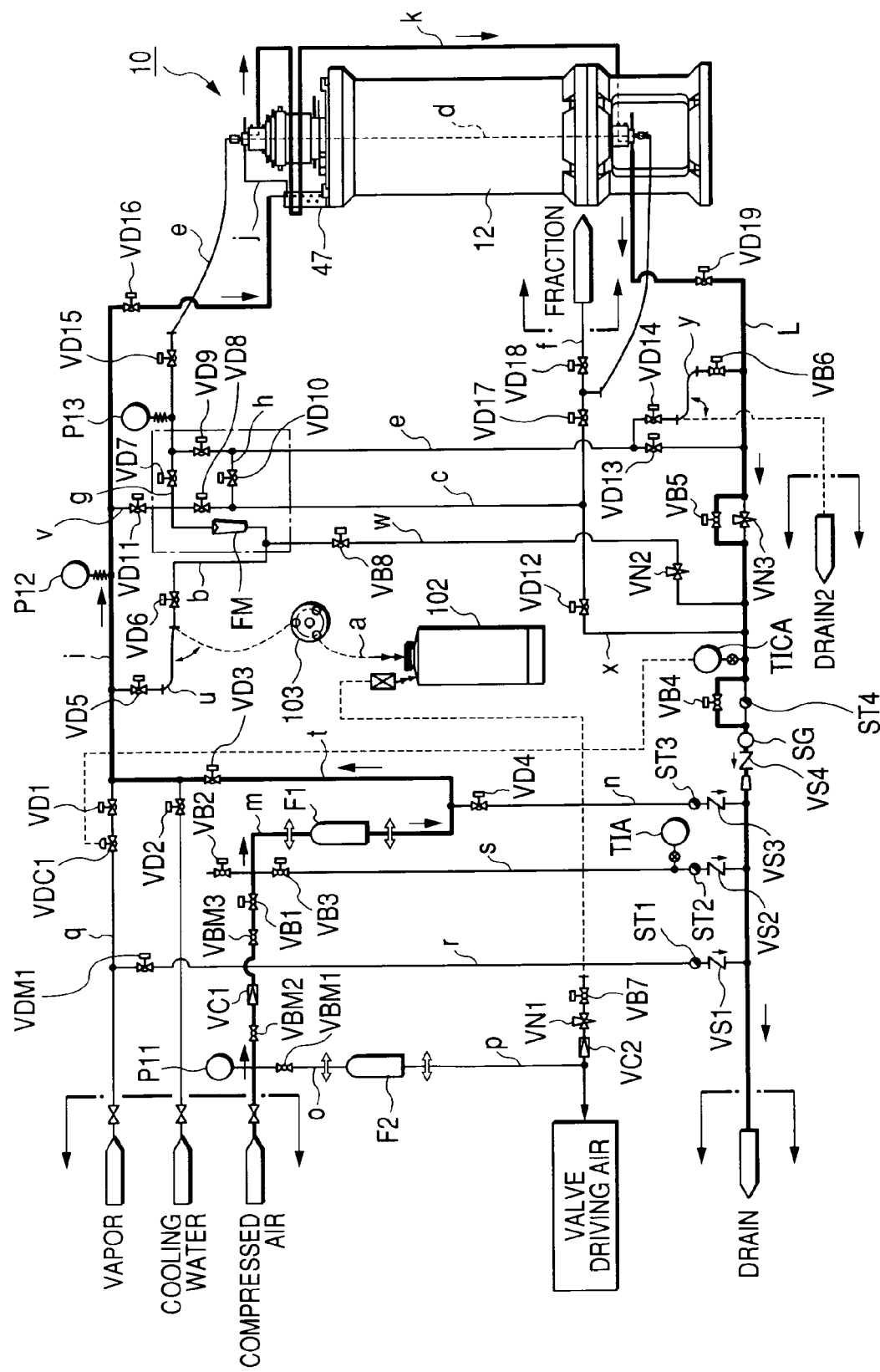
FIG. 9 is a piping diagram showing flow of air at air blowing step in the centrifugal separator according to Embodiment 1 of the invention.
Figure 10:
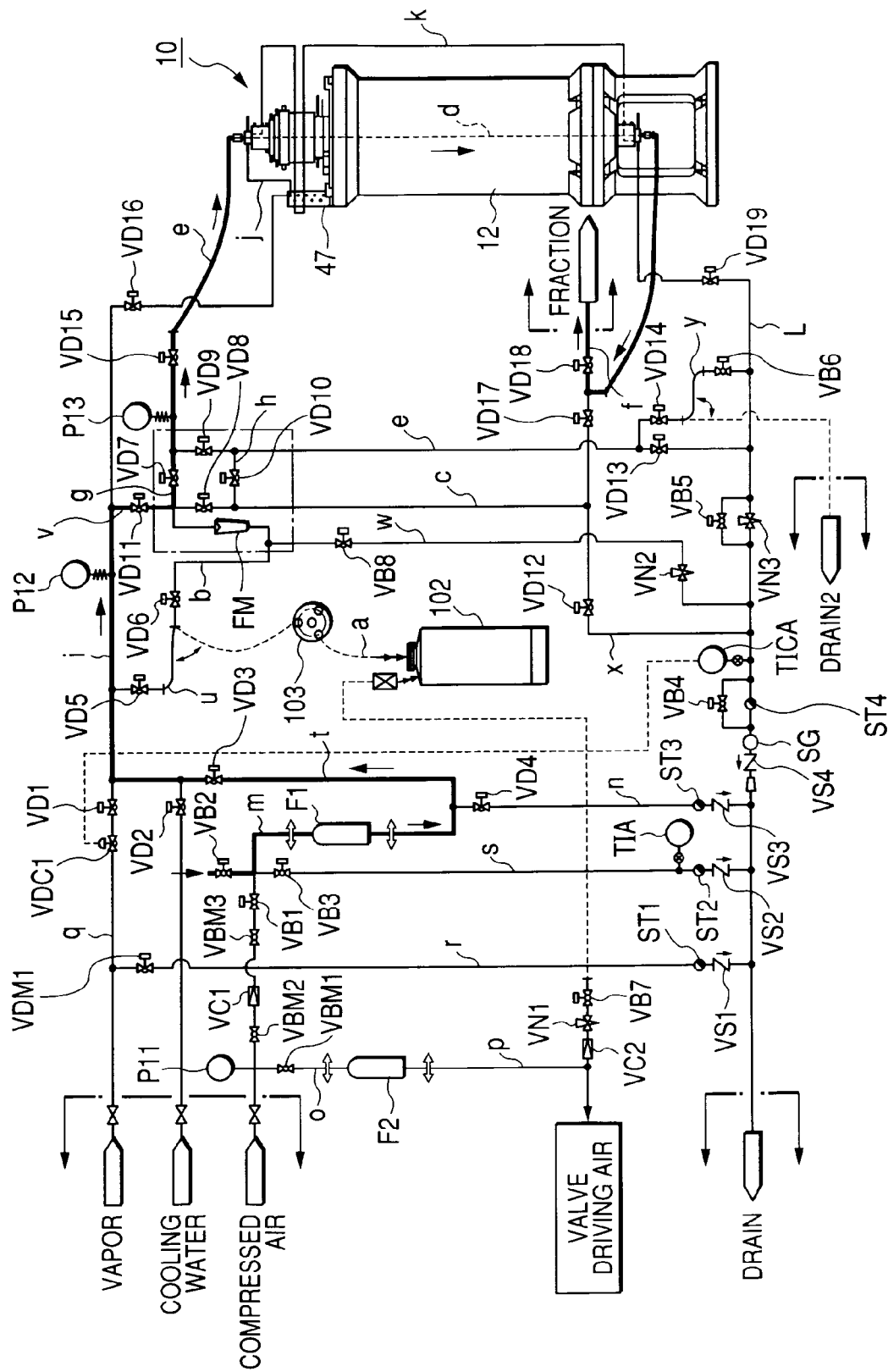
FIG. 10 is a piping diagram showing flow of a separated sample and air at a separated sample recovering step in the centrifugal separator according to Embodiment 1 of the invention.

4) Air Blowing Step:

When the sample has been centrifugally separated by the above-described centrifugally separating step, rotation of the rotor 13 and flow of cooling water are stopped, and as shown by arrow marks in FIG. 9, air from an air supplying facility the compressor or the like is made to flow to the cooling water lines i, j, k, L via the lines m, t to blow the lines m, t, j through L by air.

Further, the air blowing step is a step executed for removing cooling water and moisture remaining in the pipes prior to the successive separated sample recovering step.

5) Separated Sample Recovering Step:

When the air blowing step has been finished, the operation proceeds to the separated sample recovering step, and in the separated sample recovering step, the valve VB2 is opened in a state of closing the valve VD17 and opening the valves VD3, VD11, VD7, VD15, VD18. Then, the atmosphere flows in arrow mark directions of FIG. 10 through the lines m, t, i, v, g, e, inside of the rotor 13 at inside of the chamber 12 is opened to the atmosphere and therefore, the sample (separated sample) including particles sedimented in the rotor 13 in the centrifugal separating step is discharged to be recovered by the sample recovery tank, not illustrated, by passing a portion of the line c and the line f from the sample injecting connector 17 at the lower portion of the chamber 12 by its own weight.

Meanwhile, according to the embodiment, in the air blowing step which is a preceding step of the separated sample recovering step, the lines m, t, i through L are blown by air and therefore, in recovering the separated sample, the atmosphere smoothly passes through the air line and the cooling water line (line m, t, i, v, g, e) to firmly open inside of the rotor 13. As a result, the separated sample remaining at inside of the rotor 13 is discharged to outside of the rotor 13 to recover by its own weight.

6) Cleaning Step:

When the separated sample has been recovered by the separated sample recovering step, the operation proceed to the successive cleaning step and the sample line and the cooling water line are cleaned by distilled water.

Prior to cleaning, the line between the valve VD6 and the liquid feeding pump 103 is switched to the line u between the valves VD5 and VD6, similarly, a line on a side of the sample discharging tank (DRAIN2), not illustrated, rearward from the valve VD14 is switched to the line y.

Figure 11:
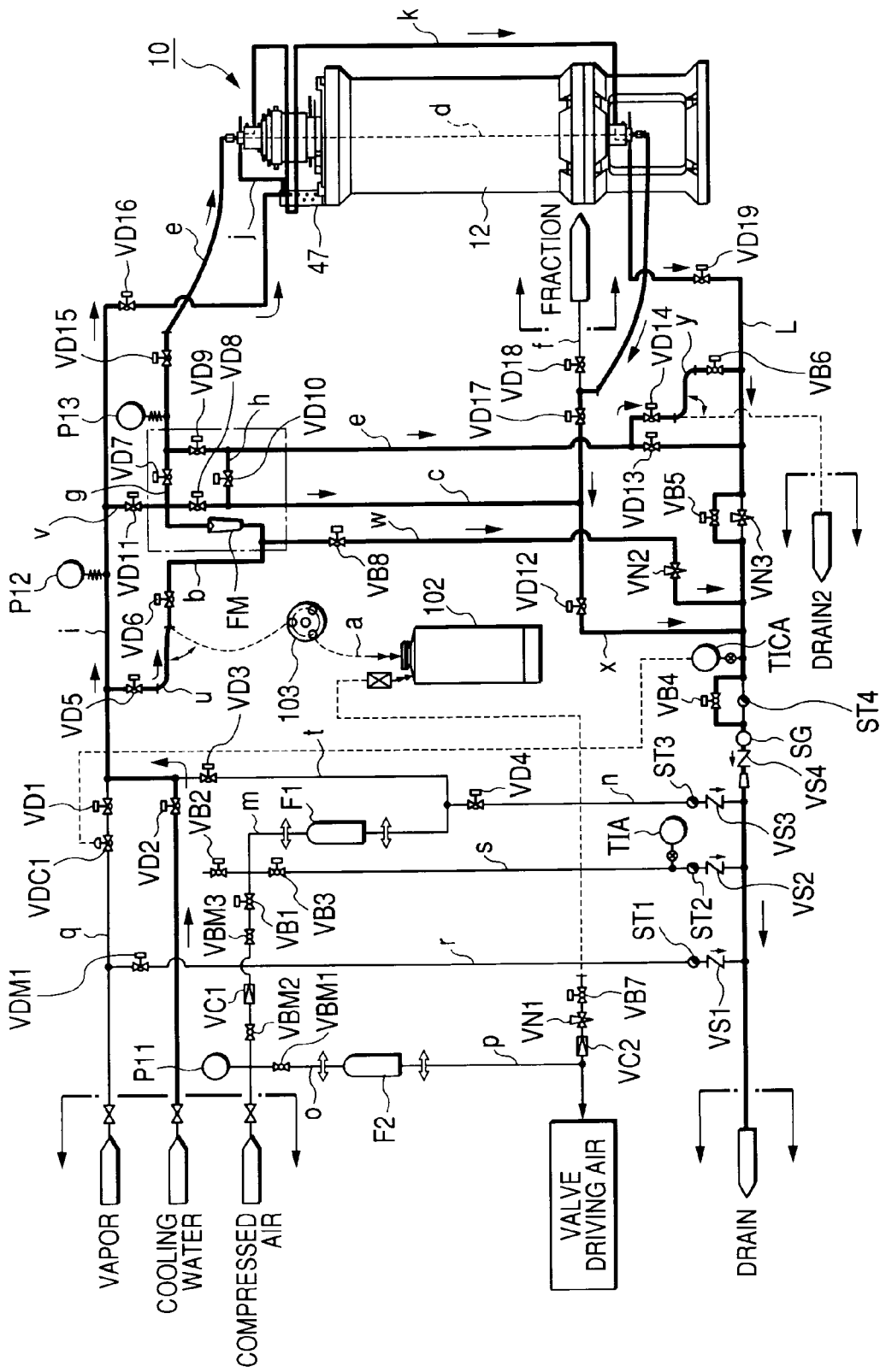
FIG. 11 is a piping diagram showing flow of distilled water in a cleaning step in the centrifugal separator according to Embodiment 1 of the invention.

In the cleaning step, as shown by arrow marks in FIG. 11, a portion of distilled water from a distilling facility, not illustrated, is made to flow from the line i to the side of the line u constituting the side of the sample line and other distilled water is made to flow to the side of the line i constituting the cooling water line as it is. Further, a portion of distilled water made to flow to the side of the line u reaches the line L via the lines b, w, reaches the line L via the lines b, c, x and the lines b, g, h, e, y, and flows downward through the line d formed in the chamber 12 from the line e, and flows in illustrated arrow mark directions in the lines c, x to reach the line L. Further, a remaining portion of distilled water flowing in the line i merges the line c via the line v, and reaches the line L by flowing from the line i through the lines j, k in illustrated arrow mark directions via the connecting portion 47. Further, distilled water reaching the line L is discharged to the drain (DRAIN).

On the other hand, a portion of distilled water flowing to the side of the line i merges distilled water flowing through the line b via the line v, other distilled water flows in illustrated arrow mark directions through the lines j, k constituting the cooling water line and is discharged to the drain (DRAIN) via the line L.

Further, the respective lines are respectively cleaned by distilled water flowing in the above-described paths, the series of operation is finished here, and the sample line and the cooling water line can be cleaned by distilled water in the state of integrating the rotor 13 to the chamber 12 after recovering the centrifugally separated sample (separated sample).

Further, in the above-described series of steps, in the pipes through which vapor, cooling water, compressed air flow, the valves provided with the pipes are opened and all of other valves are closed.

Embodiment 2

Next, Embodiment 2 of the invention will be explained in reference to FIG. 12 and FIG. 13.

The embodiment is characterized in adopting a constitution of circulating cooling water in a closed loop in the centrifugally separating step, and other constitution is similar to that of Embodiment 1, mentioned above.

Figure 12:
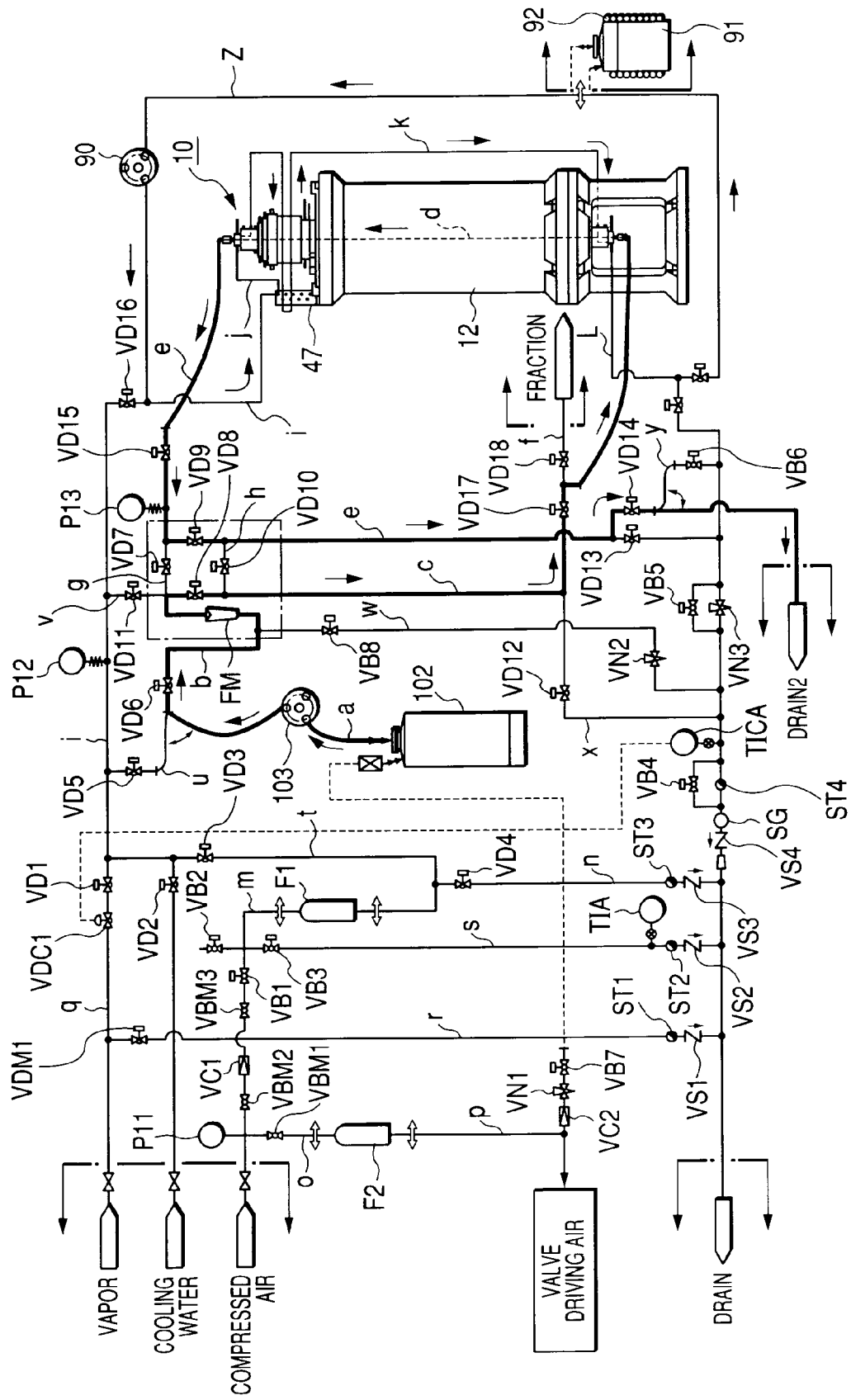
FIG. 12 is a piping diagram showing flow of a sample and cooling water at a centrifugal separating step in a centrifugal separator according to Embodiment 2 of the invention.

That is, as shown by FIG. 12, a line z branched from the line i is connected to the line L, the cooling water line of a closed loop is constituted by the lines i, z, L and the lines j, k, a cooling water pump 90 is provided and a cooling water tank 91 arranged in a sterile chamber is connected to middles of the line z, and a cooling coil 92 is wound at a surrounding of the cooling water tank 91. Further, the cold medium supplied from the refrigerator, not illustrated, is made to flow in the cooling coil 92 and cooling water flowing in the cooling water line of the closed loop is cooled by evaporating the cold medium.

Figure 13:
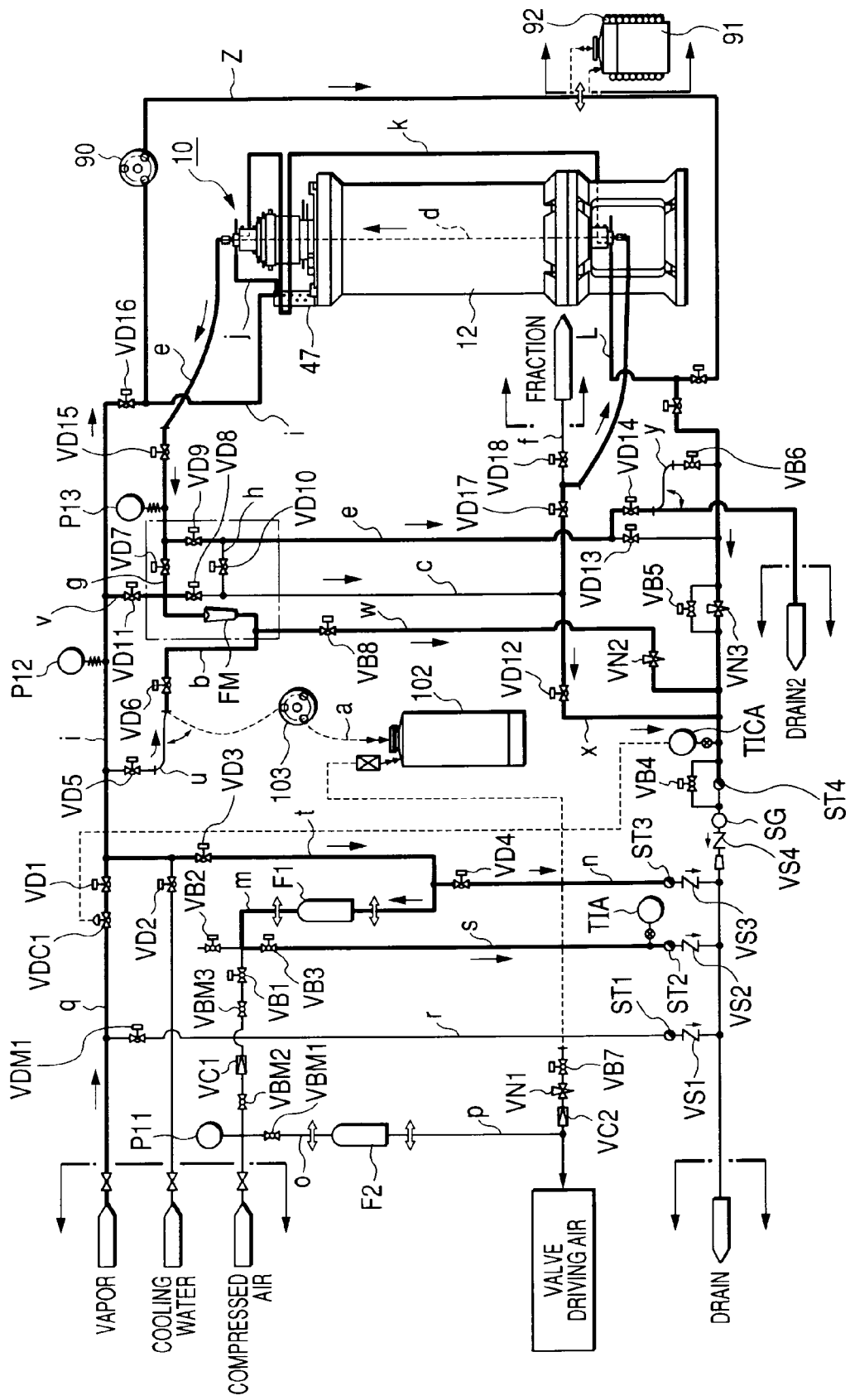
FIG. 13 is a piping diagram showing flow of vapor at a vapor sterilizing step in the centrifugal separator according to Embodiment 2 of the invention.

In the vapor sterilizing processing in the case of adopting such a constitution, in a state of removing the cooling water tank 91 from the line z, as shown by arrow marks in FIG. 13, by making vapor flows through the lines i, z, j, k, L constituting the cooling water line constituting the closed loop, the lines i, z, j though L can be sterilized similar to other lines. Further, after the sterilizing processing has been finished, as shown by FIG. 12, the centrifugally separating step may be carried out by connecting the cooling water tank 91 to the line z in the sterilized chamber.

Further, according to the embodiment, cooling water which is expensive distilled water can be circulated to use in the closed loop without discharging cooling water to out of the system and therefore, an amount of using cooling water is reduced and cost of operating the apparatus can be restrained to be low.

Meanwhile, according to the above-described embodiment, the vapor sterilizing apparatus 100 is constituted independently from the rotating apparatus portion 10 and the control apparatus portion 200 and therefore, the vapor sterilizing apparatus 100, the rotating apparatus portion 10 and the control apparatus portion 200 can be installed arbitrarily in accordance with a room of installing the centrifugal separator 1, and the vapor sterilizing apparatus 100 can be used by being combined with the rotating apparatus portion 10 and the control apparatus portion 200 at a later stage as necessary.

Further, although according to the above-described embodiments, steam at high temperature is used as the sterilizing fluid, other arbitrary sterilizing fluid of a chemical (caustic soda (sodium hydroxide), ethanol, formalin) or the like can be used.

The invention is useful for the centrifugal separator which needs the sterilizing processing for preventing virus, bacteria, or impurity or the like from being mixed to the sample.

According to the invention, in the state of integrating the rotor to the rotating apparatus portion, at least the portion with which the sample is brought into contact is sterilized by making the sterilizing fluid of vapor or the like flow through the existing sample line by the sterilizing apparatus and therefore, centrifugal separation of the sample can be realized under a complete sterile state.

According to the invention, also the cooling water line is sterilized by making the sterilizing fluid flow also to the cooling water line for supplying cooling water to the rotating apparatus portion and therefore, bacteria included in cooling water can firmly be prevented from being mixed to the sample and centrifugal separation of the sample can be carried out under a further complete sterile state.

According to the invention, expensive distilled water or the like used as cooling water is circulated to be subjected to cooling and therefore, operating cost can be reduced by reducing an amount of using cooling water.

According to the invention, at least the portion with which the sample is brought into contact is firmly sterilized by vapor or the chemical solution and bacteria can firmly be prevented from being mixed to the sample.

According to the invention, the sterilizing processing is executed while supplying oil to the seal portion or the bearing portion in the rotating apparatus portion and therefore, leakage of the sterilizing fluid from the seal portion and the bearing portion and invasion of the atmosphere can firmly be prevented and a vacuum state in the rotor chamber is maintained.

According to the invention, inside of the rotor chamber is sterilized by maintaining the inside of the rotor chamber in the vacuum state and therefore, a thermally insulating layer is formed at inside of the rotor chamber, and in the case of using, for example, vapor at high temperature as the sterilizing fluid, the rotor is swiftly heated by vapor and the rotor is sterilized efficiently.

According to the invention, the line to be processed is pressurized by air after the sterilizing processing and therefore, invasion of the atmosphere into the line to be processed is prevented and bacteria floating in the air are firmly prevented from being mixed to the line to be processed.

According to the invention, as the post processing of the sterilizing processing step, the rotor the temperature of which is elevated by being heated by, for example, vapor is cooled by cooling water and therefore, centrifugal separation of the sample which is successively executed can swiftly be executed.

According to the invention, as the preprocessing of the separated sample recovering step of recovering the centrifugally separated sample, the air line and the cooling water line are blown by air and therefore, in recovering the separated sample, the atmosphere smoothly passes through the air line and the cooling water line, inside of the rotor is firmly opened to the atmosphere, and the separated sample remaining at inside thereof is discharged to outside of the rotor by its own weight to recover.

According to the invention, after recovering the centrifugally separated sample, in the state of integrating the rotor, the sample line and the cooling water line can be cleaned by distilled water, and it is not necessary to disintegrate or attach or detach the rotor, the pipes or the like in cleaning.

According to the invention, the sterilizing apparatus is constituted independently from the rotating apparatus portion and the control apparatus portion and therefore, the sterilizing apparatus and the rotating apparatus portion and the control apparatus portion can arbitrarily installed in accordance with a room of installing the centrifugal separator, and the sterilizing apparatus can be combined with the existing rotating apparatus portion and the existing control apparatus portion to use at a later stage as necessary.

According to the invention, the control portion for controlling the sterilizing apparatus can receive various signals from the control apparatus portion and can control the sterilizing apparatus properly based on the signals.

What is claimed is:

1. A continuous flow type centrifuge comprising:
   a rotor rotatably disposed in a rotor chamber;
   a drive motor coupled to the rotor for rotating the rotor about a rotation axis;
   a sample line for supplying a sample stored in a sample tank and discharging the centrifugally separated sample from the rotor;
   a sterilizing apparatus including a sterilizing fluid source for making a sterilizing fluid flow through the sample line;
   a vacuum pump for maintaining the rotor chamber in a vacuum state when the sterilizing apparatus supplies sterilizing fluid to the rotor;
   a cooling water pipe for supplying a cooling water to the rotor;
   means for making the sterilizing fluid flow to the cooling water pipe; and
   a compressed air source and an air pipe for making an air flow through the cooling pipe to remove the cooling water and moisture remaining in the cooling pipe.

2. The continuous flow type centrifuge according to claim 1, wherein the sterilizing fluid is vapor or a chemical.

3. The continuous flow type centrifuge according to claim 1, wherein a valve is provided to supply the cooling water to the rotor after the sterilizing apparatus supplies sterilizing fluid to the rotor.

4. A continuous flow type centrifuge comprising:
   a rotating apparatus portion including a rotor rotatably disposed in a main housing;
   a drive motor coupled to the rotor for rotating the rotor about a rotation axis;
   a sample line for supplying a sample stored in a sample tank and discharging the centrifugally separated sample from the rotor;
   a sterilizing apparatus including a sterilizing fluid source for making a sterilizing fluid flow through the sample line;
   means for supplying sterilizing fluid to the rotor while supplying oil to a seal portion and a bearing portion of the rotor;
   a cooling water pipe for supplying a cooling water to the rotor;
   means for making the sterilizing fluid flow to the cooling water pipe; and
   a compressed air source and an air pipe for making an air flow through the cooling pipe to remove the cooling water and moisture remaining in the cooling pipe.

5. The continuous flow type centrifuge according to claim 4, wherein the sterilizing fluid is vapor or a chemical.

6. The continuous flow type centrifuge according to claim 4, wherein a valve is provided to supply the cooling water to the rotor after the sterilizing apparatus supplies sterilizing fluid to the rotor.

* * * * *